(12) United States Patent
Rosenquist et al.

(10) Patent No.: US 6,469,027 B1
(45) Date of Patent: Oct. 22, 2002

(54) N-METHYL-D-ASPARTATE (NMDA) RECEPTOR BLOCKERS FOR THE PREVENTION OF ATHEROSCLEROSIS

(75) Inventors: Thomas H. Rosenquist; Daniel T. Monaghan; Preston F. Gadson; Vincent J. Andaloro, all of Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/474,632

(22) Filed: Dec. 29, 1999

Related U.S. Application Data

(63) Continuation of application No. 08/850,415, filed on May 2, 1997, now Pat. No. 6,025,369.
(60) Provisional application No. 60/016,544, filed on May 3, 1996.

(51) Int. Cl.[7] .......................... A61K 31/47; C12Q 1/68; G01N 33/566
(52) U.S. Cl. ............................ 514/311; 435/6; 436/501
(58) Field of Search ............................ 514/311; 435/6; 436/501

(56) References Cited

PUBLICATIONS

Bigge, "Structural requirements for the development of potent N–methyl–D–aspartic acid (NMDA) receptor antagonists", Biochem. Pharmacol. 45(8):1547–1561 (1993).*

Tsai et al, "Promotion of vascular smooth muscle cell growth by homocysteine:a link to atherosclerosis", PNAS 91:6369–6373 (1994).*

* cited by examiner

*Primary Examiner*—Jeffrey Fredman
(74) *Attorney, Agent, or Firm*—McKee, Voorhees & Sease, P.L.C.

(57) ABSTRACT

The present invention relates to the novel finding that homocysteine affects the initiation and/or progress of atherosclerosis via a receptor-mediated growth factor effect on vascular smooth muscle cells. This growth factor effect can be inhibited by N-methyl-D-aspartate antagonists via a unique receptor that is in the NMDA receptor family. Through the use of cloning and other procedures, this homocysteine receptor can be characterized in order to develop novel pharmacologic strategies that the address the receptor for the prevention and treatment of atherosclerosis.

15 Claims, 13 Drawing Sheets

◨ CYSTOL
▦ MEMBRANE PARTICULATE
⊠ NUCLEAR

☐ NO TREATMENT
▨ 1% FBS + HOMOCYSTEINE
▨ 1% FBS + STAUROSPORINE
▨ 1% FBS + CHELEYRITHRINE

N-METHYL-D-ASPARTATE (NMDA) RECEPTOR BLOCKERS FOR THE PREVENTION OF ATHEROSCLEROSIS

CROSS-REFERENCE TO A RELATED APPLICATION

This application is a continuation of commonly owned U.S. Ser. No. 08/850,415 filed May 2, 1997, now U.S. Pat No. 6,025,369 which is a continuation in part of commonly owned U.S. Provisional application No. 60/016,544 filed May 3, 1996.

GRANT REFERENCE CLAUSE

This invention was supported at least in part by a grant from the National Institutes of Health (NIH-95-HL-01-H). The United States government has certain rights in this invention.

FIELD OF THE INVENTION

This invention relates to N-Methyl-D-Aspartate (NMDA) Receptor Blockers for the Prevention of Atherosclerosis. In addition, this invention relates to the unique homocysteine receptor and the blockage of this receptor in the prevention of atherosclerosis. This invention further relates to therapies using NMDA Receptor Blockers, including blockers for a NMDA-like receptor.

BACKGROUND OF THE INVENTION

Atherosclerosis (AS) is the principal cause of cardiovascular disease. AS is a disease of the intima of the arteries, especially of the large arteries, that leads to fatty lesions called atheromatous plaques on the inner surfaces of the arteries. The earliest stage in the development of these lesions is believed to be damage to the endothelial cells and sublying intima. The damage can be caused by physical abrasion of the endothelium, by abnormal substances in the blood, or even by the effect of the pulsating arterial pressure on the vessel wall. Once the damage has occurred, the endothelial and smooth muscle cells swell and proliferate and migrate from the media of the arteries into the lesion. Soon thereafter, lipid substances, especially cholesterol, begin to deposit from the blood in the proliferating cells, forming the atheromatous plaques.

In the later stages of the lesions, fibroblasts infiltrate the degenerative areas and cause progressive sclerosis (fibrosis) of the arteries. Still later, calcium often precipitates with the lipids to develop calcified plaques. When these two processes have occurred, the arteries are then extremely hard, and the disease is called arteriosclerosis, or simply "hardening of the arteries."

Arteriosclerotic arteries lose most of their distensibility, and because of the degenerative areas they are easily ruptured. Also, the atheromatous plaques of their surfaces causes blood clots to develop, with resultant thrombus or embolus formation. Almost half of all human beings in the United States and Europe die of arteriosclerosis. Approximately two thirds of these deaths are caused by thrombosis of one or more coronary arteries, and the remaining one third by thrombosis or hemorrhage of vessels in other organs of the body, such as in the brain which causes strokes, as well as in the kidneys, liver, gastrointestinal tract, and limbs.

An important part of this response to injury model in AS is the action of smooth muscle cells. Once the lumen of the vessel has been damaged by hypercholesterolemia, hypertension or some other pathological process, proliferation of smooth muscle cells occurs. This is followed by the formation of a connected tissue matrix, which comprises the groundwork for the atherosclerotic plaque. Smooth muscle cells are not only responsible for the formation of this matrix, but also contain the ability to express genes for a number of growth regulatory molecules, as well as receptors to growth factors. Thus, smooth muscle cells play a pivotal role in the pathogenesis of AS.

Homocysteine, a sulfur-containing amino acid, is an intermediate metabolite of methionine. Elevated plasma homocysteine, which results from an inherited disorder of methionine metabolism, is linked to an increased risk of cardiovascular disease. Homocystinuria is associated with the early onset of arteriosclerosis and frequent life-threatening thrombotic episodes, in which cerebral infarction is more common than myocardial infarction. Mudd, S. H., et al., (1985). "The natural history of homocystinuria due to cystathionine β-synthase deficiency" *Am. J. Hum. Genet.* 37:1–31.

Animal studies have shown that homocysteine is a potent inducer of atherosclerosis, causing visible vascular damage within 1 week of continuous administration. Individuals with an inborn error of homocysteine metabolism have marked hyperhomocystinemia, mental retardation, and severe atherosclerosis that usually results in death by age 15. Numerous studies have documented the association between occlusive vascular disease and elevated blood levels of homocysteine.

While it is now generally agreed that homocysteine (Hcy) is an independent risk factor for atherosclerosis, there has been less agreement on the biological basis or mechanism of action of the atherogenic effect of Hcy. A growth effect of Hcy upon vascular smooth muscle has been shown with several different approaches. For example, hypertrophy, hyperplasia and migration of smooth muscle cells are the most prominent features of atherosclerotic arteries in miniature swine with experimental hyperhomocystinemia. This is consistent with the finding of a strong positive correlation between serum Hcy concentration and carotid artery wall thickness in man, with a major increase in medial thickness. With extreme elevation of serum Hcy (e.g., in homocystinuric patients who are homozygous for a mutant non-functional cystathione-β-synthase gene), the resulting atheromata are primarily composed of vascular smooth muscle cells that produce a fibrotic lesion. These may progress to fibrolipid lesions when lipoproteins bind to the vessel matrix that is induced by Hcy. While the mechanism of this growth effect of Hcy is not well understood, there is evidence that Hcy is directly mitotic for aortic smooth muscle cells.

Tsai et al. recently have shown that Hcy is mitogenic for rat aortic smooth muscle cells in vitro, and referred to a "growth factor-like" activity of Hcy. Tsai, J. et al., (1994). "Promotion of vascular smooth muscle cell growth by homocysteine: a link to atherosclerosis," *Proc. Natl. Acad. Sci.*, 91:6369–6373. They found that Hcy induces upregulation of cyclins. The inventors have now found that Hcy also has a mitogenic effect upon avian and mammalian aortic smooth muscle cells in vitro. The inventor's data showed a growth factor effect of Hcy that appears to be receptor-mediated. This finding has led to the discovery of a novel Hcy receptor that has anatomic and physiological properties that may account for a major effect of Hcy in atherogenesis. This receptor can be blocked by antagonists in the NMDA receptor antagonist family as a new and effective way of preventing and treating atherosclerosis. Further, cloning of this receptor will allow for the development of antagonists which are even more specific for the Hcy receptor.

It is therefore a primary objective of the present invention to provide a new means of preventing and treating atherosclerosis without the side effects associated with alcohol treatment.

It is a further objective of the present invention to provide a method of treating atherosclerosis using NMDA antagonists to block the growth factor effect of homocysteine.

It is yet a further objective of the present invention to provide a means of isolating and characterizing the Hcy NMDA-like receptor.

It is still a further objective of the present invention to provide a means of cloning the homocysteine NMDA-like receptor.

It is a further objective of the present invention to identify antagonists which are specific to the Hcy receptor.

These and other objectives will become clear from the foregoing detailed description.

SUMMARY OF THE INVENTION

The present invention relates to a new method and means for treating atherosclerosis. It has now been discovered that the growth effects of homocysteine on vascular smooth muscle cells is mediated through a NMDA-like glutamate gated calcium ion channel receptor. Based on this finding, the growth effects of homocysteine can be blocked through the use of NMDA receptor antagonists.

The present invention further contemplates the cloning of the NMDA-like receptor. Knowledge of the composition of this novel homocysteine receptor will permit the development of new drugs that are specific to the homocysteine receptor, thereby yielding the anti-atherogenic effects of ethanol without the untoward side effects of ethanol ingestion.

BRIEF DESCRIPTION OF THE DRAWINGS

FIGS. 3A, 3B and 3C are RNA blot analyses of c-fos and c-myb mRNA isolated from N-VSMC cultures. Cultures were incubated in the absence and presence of 200$\mu$M H[cys] for 0, (lane 1); 15 min, (lane 2); 30 min, (lane 3); 45 min, (lane 4) and 60 min, (lane 5); and analyzed for c-fos expression. In FIG. 3B, the time course of c-myb MRNA induction in the presence of 200$\mu$M H[cys] for 0 h, (lane 1); 8 h, (lane 2); 16 h, (lane 3); 24 h, (lane 4). The c-fos transcripts were analyzed by northern blot and normalized to $\beta$ actin expression. The amount of c-myb mRNA levels were normalized to estrogen receptor (ER) transcripts as determined by RT-PCR. FIG. 3C demonstrates a dose dependent increase in cMyb protein after treating N-VSMC with 30 and 100 $\mu$M Hcys in the presence 300 $\mu$Ci/ml [$^{35}$H] methionine/cysteine. The amount of c-myb mRNA levels were normalized to estrogen receptor (ER) transcripts as determined by RT-PCR. The amount of specific radiolabeling in the autoradiograph was quantified by scanning densitometry. The size of the c-Myb protein is 75 kilodaltons. The 75 kilodalton band is defined as c-Myb because immunoprecipitation of this protein was not detected in the presence of synthetic polypeptide [Ile-Gln-Arg-His-Tyr-Asp-Glu-Asp-Pro-Glu-Lys-Glu-Arg-Ile-Lys-Glu-Leu; encoded by sequences 1080–1133].

DETAILED DESCRIPTION OF THE INVENTION

Figure 1:
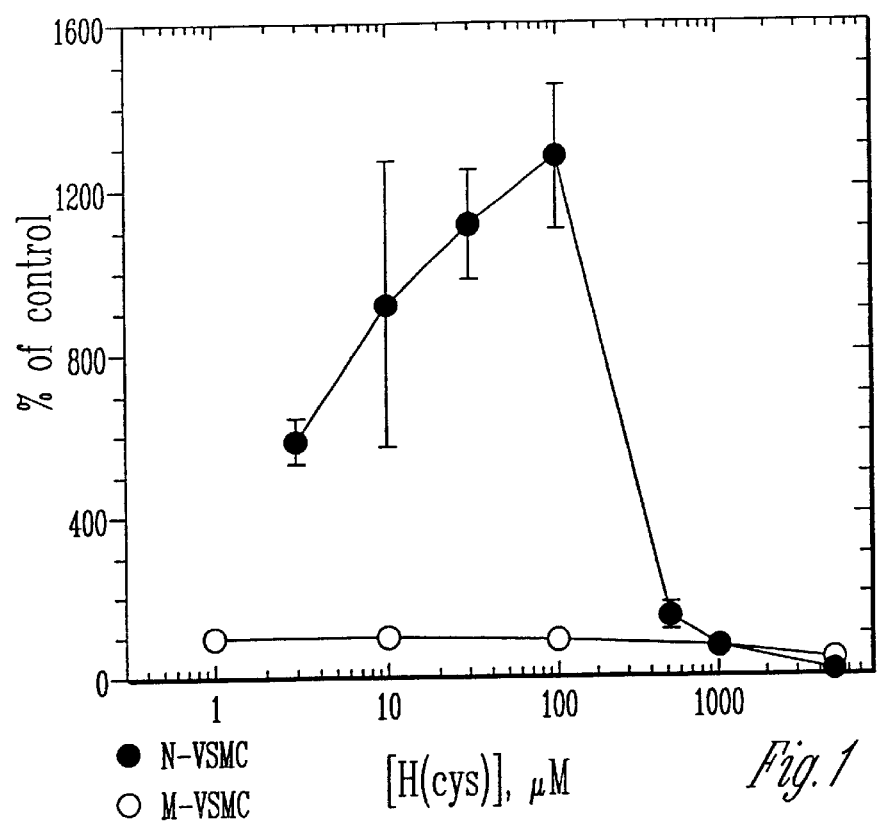
FIG. 1 is a graph illustrating homocysteine's effects on the growth of VSMC cultures. Confluent N-VSMC cultures were growth arrested by incubating cells with M199 medium containing 1 $\mu$g/ml BSA for 48 h, exposed to various concentrations of H[cys] (0.01-4000$\mu$M) for 30 h, pulse labeled for 6 h with 2 $\mu$Ci/ml [$^3$H]-thymidine, and cell monolayers were washed twice with cold (0° C.) 10% trichloroacetic acid (TCA). The amount of [$^3$H]-thymidine incorporation was determined by scintillation spectrophotometry. Results are shown as the means of ±S.D.

Published data has shown that an elevated level of the amino acid homocysteine is an independent risk factor for the development of cerebral, coronary and peripheral atherosclerosis and coronary artery disease. It has further been shown by others that ethanol ingestion inhibits the progress of atherosclerosis and coronary artery disease in a dose-related fashion. In each of these cases, neither the biologic nor the molecular mechanism has been identified. It has now been discovered that the promoting effect of homocysteine is related to the blocking effect of ethanol. These findings can be used to plot a unique atherosclerosis prevention strategy.

The development of complicated arteriosclerotic plaque in humans involves proliferation of vascular smooth muscle cells and the accumulation of extracellular matrix. Because of the significance of vascular smooth muscle cell (VSMC) proliferation and matrix production during morphogenesis of blood vessels and in vascular diseases, many studies have examined the role of serum-associated mitogens such as platelet derived growth factor (PDGF) and transforming growth factor beta (TGF-β1) in these processes. However, only one report has implicated direct effects of homocysteine on vascular cells. Tsai et al. have shown that homocysteine can stimulate VSMC growth and inhibit the proliferation of endothelial cells by an unknown mechanism. Tsai, J. C., et al. (1994). Promotion of vascular smooth muscle cell growth by homocysteine: A link to atherosclerosis. *Proc. Natl. Acad. Sci. USA*, 91:6369–6373. Earlier reports have suggested that the central nervous system symptoms of patients with homocystinuria could be explained by NMDA type glutamate receptor overstimulation by L-homocysteic acid. McCully, K. S., (1971). Homocysteine metabolism in scurvy, growth and arteriosclerosis, *Nature* 231:391–394. The investigators suggest that homocysteine is converted to homocysteic acid. However, there is no evidence to indicate that such a conversion occurs in patients with homocystinuria.

The present inventors have determined that the mechanism for the homocysteine effect on VSMC proliferation occurs through a novel receptor/transport system. Their test results have demonstrated that homocysteine activates a specific receptor/transporter-like factor that is coupled to diacylglycerol production and protein kinase C activation (PKC) in VSMC. The inventors have partially characterized the pharmacology of the homocysteine receptor and have partially cloned the gene for the homocysteine receptor from human vascular smooth muscle cells. Their studies indicate that the homocysteine receptor is a member of the N-methyl-D-aspartate (NMDA) family, but is not actually an NMDA receptor.

Although the relationship between elevated levels of homocysteine and coronary artery disease was previously known in the art, the prior art concluded only that all levels of homocysteine were harmful. Brattstrom, A. et al. (1992). Hyperhomocystinemia in stroke: prevalence, cause, and relationships to type of stroke and stroke risk factors, *Eur J Clin Invest* 22:214–221. The inventors have discovered, however, that homocysteine has normal function as a growth factor. Homocysteine has been shown to stimulate VSMC growth and inhibit the proliferation of endothelial cells. This homocysteine mediated growth effect is inhibited by certain calcium channel blockers.

The inventors have shown that Hcy induced c-fos and c-myb and increased DNA synthesis 5-fold in neural crest derived smooth muscle cells. The Hcy effect on VSMC proliferation was inhibited by MK-801, a non-competitive antagonist of the NMDA receptor and by CGS 19755, a competitive antagonist of the NMDA receptor. For these reasons, it was determined that Hcy binds an NMDA-like receptor in vascular smooth muscle cells.

The inventors have further shown that the pharmacological effect of homocysteine in VSMC is completely blocked by low concentrations of ethanol, consistent with the low levels that inhibit atherogenesis. From this data, it may be concluded that drugs in the general family of NMDA receptor blockers are capable of blocking the atherogenic effect of homocysteine. This constitutes a unique application of these compounds. NMDA receptor genes is an ion channel which is activated by glutamate and aspartate, both of which are present in the CNS. The channel is highly permeable to sodium potassium and calcium ions. The role of NMDA receptors have received considerable attention, due to their critical role in synaptic plasticity. Furthermore, knowledge of the composition of this novel homocysteine receptor through the use of cloning will permit the development of new drugs that are specific to the homocysteine receptor, thereby yielding the anti-atherogenic effect of ethanol without the untoward side effects of ethanol ingestion.

The invention thus comprises a new class of drugs for the treatment and prevention of atherosclerosis. These drugs act to inhibit the cell biochemical and physiological actions of homocysteine activated homocysteine receptor. As exemplified herein one class of drugs which effectively accomplish this objective include those which are NMDA receptor blockers.

NMDA receptors mediate synaptic transmission and neural plasticity in the mammalian central nervous system. (Monaghan, D, "The excitatory amino acid receptors: their classes, pharmacology, and distinct properties in the function of the central nervous system", *Annu Rev Pharmacol Toxicol,* 29 (1989) 365–402 availability; Collingridge, G, "Excitatory amino acid receptors in the vertebrate central nervous system", *Pharmacol Rev,* 41 (1989) 143–210 availability; McBain, C, "N-methyl-D-aspartic acid receptor structure and function", *Physiol Rev,* 74 (1994) 723–60 availability). Recent evidence has shown that NMDA receptors are differentially expressed during development (Sheng, M., "Changing subunit composition of heteromeric NMDA receptors during development of rat cortex", *Nature,* 368 (1994) 144–7), and they also mediate brain development by stabilizing converging synapses (Scheetz, A., "Modulation of NMDA receptor function: implications for vertebrate neural development", *Faseb J,* 8 (1994) 745–52), stimulating cerebellar granule cell migration (Hitoshi, K., et al., "Modulation of neuronal migration by NMDA receptors", *Science,* 1993, 260:95–97; Farrant, M, "NMDA-receptor channel diversity in the developing cerebellum, *Nature,* 368 (1994) 335–9; Rossi, D, "The developmental onset of NMDA receptor-channel activity during neuronal migration, *Neuropharmacology,* 32 (1993) 1239–48) and development (Burgoyne, R, "Neurotrophic effects of NMDA receptor activation on developing cerebellar granule cells", *J Neurocytol,* 22 (1993) 689–95), and can induce long term depression (Battistin, T, "Developmental shift from long-term depression to long-term potentiation at the mossy fibre synapses in the rat hippocampus", *Eur J Neurosci,* 6 (1994) 1750–5; Komatsu, Y, "Long-term modification of inhibitory synaptic transmission in developing visual cortex", Neuroreport, 4 (1993) 907-10; Tsumoto, T, "Long-term potentiation and depression in the cerebral neocortex", *Jpn J Physiol,* 40 (1990) 573-93) and apoptosis (Finiels, F, "Induction of neuronal apoptosis by excitotoxins associated with long-lasting increase of 12-O-tetradecanoylphorbol 13-acetate-responsive element-binding activity", *J Neurochem,* 65 (1995) 1027–34; Ankarcrona, M, Calcineurin and mitochondrial function in glutamate-induced neuronal cell death", *FEBS Lett,* 394 (1996) 321–4). NMDA receptors are also known contribute to epileptiform activity and neuronal cell in both developing brain (Wasterlain, C, "Seizures, brain damage and brain development", *Brain Dev,* 16 (1994) 279–95; McDonald, J, "Excitatory amino acid neurotoxicity in the developing brain", *NIDA Res Monogr,* 133 (1993) 195–205; Janssen, R, "Glutamate neurotoxicity in the developing rat cochlea is antagonized by kynurenic acid and MK-801, *Brain Res,* 590 (1992) 201–6) as well as excitatory cell death in a number of adult pathological conditions (Greenamyre, J, "Excitatory amino acids and Alzheimer's disease", *Neurobiol Aging,* 10 (1989) 593–602 availability; Meldrum, B, "Excitatory amino acid neurotoxicity and neurodegenerative disease", *Trends Pharmacol Sci,* 11 (1990) 379–87 availability; Clark, S, "The NMDA receptor in epilepsy", 2 edn., Oxford University Press, Oxford, 1994, 395–427 pp.; Doble, A, "Excitatory amino acid receptors and neurodegeneration", Therapie, 50 (1995) 319–37).

As the result of involvement of excitatory amino acid receptors, including NMDA receptors, in neurodegenerative diseases, specific NMDA antagonists have recently emerged in the clinical research (Lipton, S, "Prospects for clinically tolerated NMDA antagonists: open-channel blockers and alternative redox states of nitric oxide", *Trends Neurosci,* 16 (1993) 527–32) for the potential treatment of stroke, CNS trauma (Faden, A, "Pharmacological strategies in CNS trauma", *Trends Pharmacol Sci,* 13 (1992) 29–35), epilepsy (Thomas, R, "Excitatory amino acids in health and disease", *J Am Geriatr Soc,* 43 (1995) 1279–89; Perucca, E., "The clinical pharmacology of the new antiepileptic drugs", *Pharmacol Res,* 28 (1993) 89-106), pain (Elliott, K, "N-methyl-D-aspartate (NMDA) receptors, mu and kappa opioid tolerance, and perspectives on new analgesic drug development", Neuropsychopharmacology, 13 (1995) 347–56), Huntington's disease (Purdon, S, "Huntington's disease: pathogenesis, diagnosis treatment", *J Psychiatry Neurosci,* 19 (1994) 359–67), AIDS dementia (Lipton, S, "Neuronal injury associated with HIV-1 and potential treatment with calcium-channel and NMDA antagonists", *Dev Neurosci,* 16 (1994) 145–51; Lipton, S, "AIDS-related dementia and calcium homeostasis", *Ann N Y Acad Sci,* 747 (1994) 205–24), and Alzheimer's (Barry, S, "Clinical implications of basic neuroscience research. II: NMDA receptors and neurotrophic factors", *Arch Phys Med Rehabil,* 72 (1991) 1095–101) and Parkinson's (Ossowska, K., "The role of excitatory amino acids in experimental models of Parkinson's disease", *N Neural Transm Park Dis Dement Sect,* 8 (1994) 39–71) diseases (Rogawski, M., "Therapeutic potential of excitatory amino acid antagonists: channel blockers and 2,3-benzodiazepines", *Trends Pharmacol Sci,* 14 (1993) 325–31). In vivo treatment with some of these agents manifest PCP-like psychotomimetic effects. Hence, research has been underway to discover and develop more therapeutically useful and less toxic drugs (Willetts, J., "The Behavioral pharmacology of NMDA receptor antagonists", *Trends Pharmacol Sci,* 11 (1990) 423–8).

One of these classes include Ro-01-6794/706 or dextrorphan ("Safety, Tolerability and pharmacokinetics of the N-methyl-D-aspartate antagonist Ro-01-6794/706 in patients with acute ischemic stroke", The Dextrorphan Study Group and Hoffmann-La Roche, *Ann N Y Acad Sci,* 765 (1995) 249–61; discussion 298), and dextromethorphan, a widely used over the counter antitussive (Irwin, R. "Appropriate use of antitussives and protussives", A practical review, Drugs, 46 (1993) 80–91) which also is an NMDA channel blocker (Fekany, J., "Dextromethorphan inhibits NMDA-induced convulsions", *Eur J Pharmacol,* 151 (1988) 151-4; Choi, D., "Dextrorphan and levorphanol selectively block N-methyl-D-aspartate receptor-mediated neurotoxicity on cortical neurons", *J Pharmacol Exp Ther,* 242 (1987) 713–20) which may be a clinically useful neuroprotective (Steinberg, G., "Dextromethorphan alters cerebral blood flow and protects against cerebral injury following focal ischemia", *Neurosci Lett* 133 (1991) 225–8). Therapeutically tolerated doses of roughly 30 mg q.i.d. orally are used for the over the counter antitussive action, and to-90 mg q.i.d. orally for clinical treatment of brain ischemia (Albers, G, "Tolerability of oral dextromethorphan in patients with a history of brain ischemia", *Clin Neuropharmacol,* 15 (1992) 509–14). Side effects at high doses of dextromethorphan included drowsiness, nausea, and decreased coordination. Toxic high doses of dextromethorphan have been described (Wolfe, T, "Massive dextromethorphan ingestion and abuse", *Am J Emerg* Med, 13 (1995) 174–6; Hinsberger, A., "Cognitive deterioration from long-term abuse of dextromethorphan: a case report", *J Psychiatry Neurosci,* 19 (1994) 375–7); Loscher, W, "Differences in anticonvulsant potency and adverse effects between dextromethorphan and dextrorphan in amygdala-kindled and non-kindled rats" *Eur J Pharmacol*, 238 (1993) 191–200). Other currently used NMDA receptor antagonists include amantadine and ketamine.

Hundreds, if not more, other potentially clinically useful NMDA antagonists have been studied (Jane, D, "Agonists and competitive antagonists: structure-activity and molecular modelling studies", 2 edn., Oxford University Press, Oxford, 1994, 31–104 pp; Andaloro, V, "Pharmacology of NMDA receptor subtypes", *Society for Neuroscience Abstracts*, 604 (1996); Bigge, C, "Structural requirements for the development of potent N-methyl-D-aspartic acid (NMDA) receptor antagonists", *Biochem Pharmacol*, 45 (1993) 1547–61; Ornstein, P., "The development of novel competitive N-methyl-D-aspartate antagonists as useful therapeutic agents: *Discovery of LY274614 and LY233536*", Raven Press, New York, 1991, 415–423 pp), and some are even orally available, including some derivatives EAB-515 (Li, J., "Potent, orally active, competitive N-methyl-D-aspartate (NMDA) receptor antagonists are substrates for a neutral amino acid uptake system in Chinese hamster ovary cells", *J Med Chem*, 38 (1995) 1955–65 availability; Lowe, D., "The pharmacology of SDZ EAA 494, a competitive NMDA antagonist", *Neurochem Int*, 25 (1994) 583–600 availability), memantine (Parsons, C, "Comparison of the potency, kinetics and voltage-dependency of a series of uncompetitive NMDA receptor antagonists in vitro with anticonvulsive and motor impairment activity in vivo", Neuropharmacology, 34 (1995) 1239–58; Kornhuber, J., "Amantadine and memantine are NMDA receptor antagonists with neuroprotective properties", *J Neural Transm Suppl*, 43 (1994) 91–104; Wenk, G., "MK-801, memantine and amantadine show neuroprotective activity in the nucleus basalis magnocellularis" *Eur J Pharmacol*, 293 (1995) 267–70), and ketamine (Parsons, C., "Comparison of the potency, kinetics and voltage-dependency of a series of uncompetitive NMDA receptor antagonists in vitro with anticonvulsive and motor impairment activity in vivo", Neuropharmacology, 34 (1995) 1239–58; Sagratella, S., "NMDA antagonists: antiepileptic-neuroprotective drugs with diversified neuropharmacological profiles", *Pharmacol Res*, 32 (1995) 1–13; Porter, R., "Regional variations in the pharmacology of NMDA receptor channel blockers: implications for therapeutic potential", *J Neurochem*, 64 (1995) 614–23 availability). Some of these are approved for use, several others are in clinical trials, or might be in the future, for the treatment of neurodegenerative disease, epilepsy, stroke, and the other disease states described earlier. Many more are sure to come in the future, as well, and some may not even have structures anything like those already described.

References which disclose other NMDA receptor blockers as well as assays for identifying an agent that acts as such a blocker and toxicity studies for pharmacologic profiles are disclosed in the foregoing and following articles which are all hereby incorporated in their entirety by reference. (Jia-He Li, et al., *J Med Chem* (1995) 38, 1955–1965; Steinberg et al., *Neurosci Lett*, 133 (1991) 225–8; Meldrum et al., *Trends Pharmacol Sci*, 11 (1990) 379–87; Willetts et al., *Trends Pharmacol Sci*, 11 (1990) 423–8; Faden et al., *Trends Pharmacol Sci*, 13 (1992) 29–35; Rogawski, *Trends Pharmacol Sci*, 14 (1993) 325–31; Albers et al, *Clinical Neuropharm*, 15 (1992) 509–514; Wolfe et al., *Am J Emerg Med*, 13 (1995) 174–6; Bigge, *Biochem Pharmacol*, 45 (1993) 1547–61.)

Some NMDA receptor blockers which are useful in accordance with the present invention include but are not limited to NMDA Receptor Glycine Site Antagonists having the general formulas:

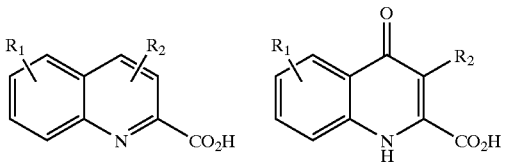

wherein $R_1$ is H, Cl, Br, I, F, HO, MeO, EtO, Me, or Et; and $R_2$ is H, OH, COOH, SH, p-OH—Ph, Me, Ome, Sme, Cl, Br, or F;

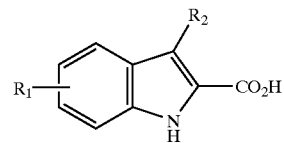

wherein $R_1$=H, Cl, Br, Cl, I, F, HO, MeO, EtO, Me, or Et; and $R_2$=H, OH, COOH, SH, p-OH—Ph, Me, Ome, Sme, Cl, Br., F, $CH_2CONH$ $(C_3H_7)$, $CH_2CH_2COOH$.

Other NMDA Receptor Antagonists which may be used in the present invention include opioid-like drugs which include levopropoxyphene and morphinans which include dextromethorphan, which have the general formula:

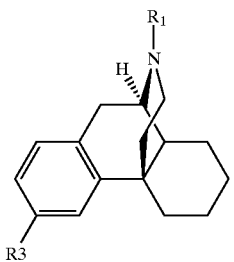

In a preferred embodiment, dextromethorphan, $R_1$ is methyl and $R_3$ is methoxy; for dextrorphan $R_3$ is hydroxy.

Memantine, and its analogs: (Including amantadine, where $Rl_{1-5}$ are all Hydrogen)

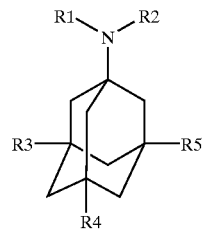

Levopropoxyphene and it's analogs:

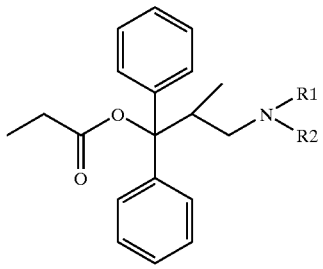

Ketamine and it's analogs:

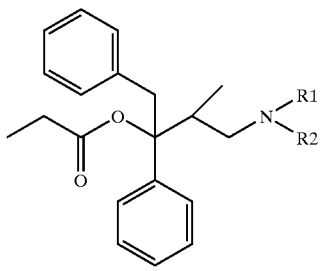

Remacemide and it's analogs:

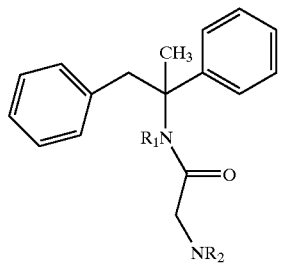

MK-801 and it's analogs:

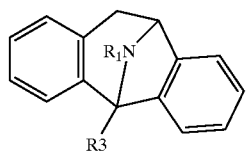

Carbamazepine and it's analogs:

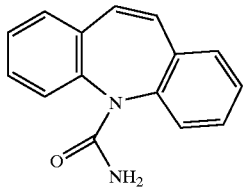

Valproic acid and analogs:

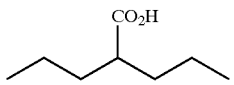

R moieties can be substituent which confers activity according to the methods and assays disclosed herein. Examples of such moieties include but are not limited to $R_1$ or $R_2$=H, an alkyl group, nPr, iPr, or any other acceptable substitute and $R_{3-5}$=H, OH, methyl, ethyl, n-Pr, iPr, Cl, I, F, MeO, EtO, AcO, Ac, or any other acceptable substitute.

See also Biggs, C. F., et al., "Agonists, antagonists, and modulators of the N-methyl-D-aspartic acid (NMDA) and α-amino-3-hydroxy-5-methyl-4-isoxazolepropanoic acid (AMPA) subtypes of glutamate receptors", *Curr. Opin. Ther. Pat.*, (1993) 3:951–989.

Assays for identification of active NMDA receptor antagonists are known in the art and disclosed in any of the references cited and incorporated herein. The simplest and most recognized assay is the use of radiolabeled ligands in a ligand binding assay.

Using a microcentrifugation assay, [$^3$H]D-AP5 was the first ligand which was shown to label selectively NMDA receptors (Oliverman et al., 1984, 1988a,b) and allowed routine screening of available compounds. Specific binding using washed membranes prepared from a crude synaptosomal fraction of rat cerebral cortex represented about 40 per cent of total binding and [$^3$H]D-AP5 appeared to label a single population of sites with $K_D$ and $B_{max}$ values of about 0.5 μM and 4 pmol/mg protein respectively. [$^3$H]L-Glutamate labels sites in addition to NMDA receptors. However, at about the same time as [$^3$H]D-AP5 was introduced as an NMDA receptor ligand, it was shown that by using a highly purified membrane preparation, post-synaptic densities, almost all of the specific binding of [$^3$H]L-glutamate was to NMDA receptors (Fagg and Matus 1984; Foster and Fagg 1987; Fagg and Baud 1988). Alternatively, [$^3$H]L-glutamate can still be used successfully to label NMDA receptors in a less purified synaptic plasma membrane fraction where there is a high proportion of binding to non-NMDA receptor sites, by defining and limiting analysis to the NMDA-sensitive component of [$^3$H]L-glutamate binding (Monaghan and Cotman 1986; Monahan and Michel (1987)).

In a preferred embodiment the NMDA receptor blocker of the invention is one which is orally available such as dextromethorphan.

One important feature of this invention is that the NMDA receptor antagonists in the method of the invention do not

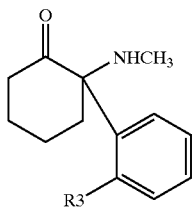

need to cross the blood brain barrier to exert their effect. This avoids several of the side effects traditionally associated with NMDA receptor blockers, some of which are traditionally opioid like compounds with narcotic like properties.

As shown in the Examples set forth below, both competitive and non-competitive NMDA antagonists successfully block the growth effects of homocysteine.

As used herein the term NMDA receptor blocker includes any compound which causes inhibition of the NMDA receptor. This includes both competitive and non-competitive antagonists as well as prodrugs which are metabolized to NMDA antagonists upon administration, as well as all analogs of such compounds shown by the assays herein to be active NMDA antagonists.

In general, in addition to the active compounds i.e. the NMDA antagonists, the pharmaceutical compositions of this invention may contain suitable excipients and auxiliaries which facilitate processing of the active compounds into preparations which can be used pharmaceutically. Oral dosage forms encompass tablets, dragees, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl-cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffinhydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers.

In addition to administration with conventional carriers, active ingredients may be administered by a variety of specialized delivery drug techniques which are known to those of skill in the art, such as portable infusion pumps.

As used herein the term "an effective amount" shall mean an amount of an NMDA receptor blocker sufficient to block the atherogenic effect of homocysteine as determined by the methods and protocols disclosed herein.

The invention further contemplates the cloning of the homocysteine receptor in order to determine the composition of the receptor. Once the receptor is characterized, antagonists which are specific to the homocysteine receptor can be developed to even more effectively block the growth effects of homocysteine and possibly decrease any side effects associated with the use of NMDA antagonists.

Hcy has recently been shown to act as a mitogen for thoracic aorta (ectomesenchymal) VSMC in vitro. To determine whether Hcy had a growth effect on VSMC, the inventors conducted a study upon ectomesenchymal VSMC in embryos as set forth below.

EXAMPLE 1

Growth Effect of Homocysteine on Embryonic Chicken Vascular Smooth Muscle Cells

Materials and Methods

Smooth Muscle Culture: The thoracic (N) and abdominal (M) aorta of normal 16 and 18-day embryos were cleaned of fat, and the intima-media was isolated from the adventitia. The intima-media was enzymatically dispersed into a single cell suspensions by a combination of collagenase and elastase followed by trypsin. VSMC were placed in primary culture at a constant density of $2 \times 10^4$ cells/cm$^2$ in multiwell plates or 100 mm culture plates in Medium 199 supplemented with 10% fetal bovine serum (FMS) and 2 mM glutamine, in an atmosphere of 95% air: 5% $Co_2$ at 37° C. Primary cultures were grown for 7 days before they were seeded into first passage at the same cell density and grown to confluence. Experiments were carried out between passages 3–6. Experimental conditions for all cells included 48 h in Medium 199 supplemented with 1% FBS prior to initiating and experiment.

DNA Synthesis: Growth factors were added directly to quiescent VSMCs in Medium 199 as described above. The cells were pulsed between 4–6 h with a final concentration of 2–5 $\mu$Ci/ml [$^3$H]thymidine added at the times and for the periods indicated in the figure legends. The cells were washed, and the incorporation of [$^3$H]thymidine into acid insoluble material was determined as previously described. Den-Heijer, M. et al. (1996), Hyperhomocystinemia as a risk factor for deep-vein thrombosis. *N. Eng. J. Med.* 334(12):759–762.

RNA Blot Analysis: Total RNA was isolated from VSMC derived from thoracic and abdominal aorta by homogenization, and lysis with guanidinium isothiocyanate was followed by phenol-chloroform extraction. Ten micrograms of total RNA per lane was separated in a 1.5% agarose-formaldehyde gel, and the RNA was transferred by capillary transfer to a 0.45 $\mu$m nylon membrane. Filters were hybridized as previously with cDNAs labeled with [$^{32}$P] deoxycytidine5'-triphosphate to specific activities of approximately 2×109 cpm/$\mu$g using a random prime labeling kit (Boehringer Mannheim Biochemicals, Indianapolis, Ind.). The probes included chicken c-fos, Bactin, estrogen receptor (ER) and c myb.

Reverse Transcriptase-Polymerase Chain Reaction: Reverse transcription of 4 to 10,000 nanograms (ng) of RNA using 10 picomoles (pm) of hexamer primers was performed for 90 minutes (min) at 37° C. using 200 units superscript reverse transcriptase (Gibco BRL), in 50 mM Tris, pH, 8.2, 75 Mm KC1, 3 mM MgCl$_2$, 10 mM dithiothreitol (DTT), 1 unit/$\mu$l RNasin (Promega), and 1 mM each of DATP, dCTP, dGTP, and dTTP. The samples were heated at 95° C. for 5 min to terminate the reverse transcription. The resulting cDNA was treated with 1 unit of deoxyribonuclease-free ribonuclease at 37° C. for 20 min. A 5% fraction of the cDNA was subjected to PCR using c-myb upstream (5'ggTCCTTTgAAgATgCTgCC3') and downstream (5'CATCACCAgAgTCCgggTTg3') primers; estrogen receptor (ER) (5'ggACTgCCAgCTgCCgATCTT3') and (5'CTCACgAATgTggCgCCT3') primers; $\beta$ actin (5'AAgAggTAATCCTgACCCCTgAA3') and (5'ACCCTgACCATCAgggAgTTCA3') primers. PCR was performed using 0.25 $\mu$M of each primer, 3 $\mu$M cDNA, 0.2 mM of each deoxynucleotide triphosphate, 75 mM KC1, 1.5 mM MgCl$_2$ and 0.5 unit Taq polymerase (Perkin Elmer; Cetus) in 10 mM Tris-HC1, pH 8.3 with total volume of 100 $\mu$l. Thirty cycles of the following PCR sequence was carried out in a Stratagene Gradient Thermocycler (Stratagene): 92° C. for 1 min, for denaturation; 50–60° C. for 1 min, for annealing, depending on the primers; 72° C. for 1.5 min per kilobase (Kb) for extension. PCR products were analyzed by electrophoresis in 1.5% agarose gels stained with ethidium bromide. PCR amplifications of all target templates and controls were run in parallel or on the same sample. The resulting PCR products from the cDNAs were 400 bp for c-myb, 550 bp for $\beta$ actin and 60 bp for ER.

Cell Labeling and Immunoprecipitation: Cells were grown to confluence and serum starved in Medium 199 containing 1 mg per ml of bovine serum albumin for 48 h. Following stimulation with various concentrations of H[cys] (0.01–100 $\mu$M) in the presence of 300 $\mu$Ci/ml [$^{35}$S] methionine/cysteine, cell medium was removed and cells rinsed twice with ice cold PBS (Ca$^{+2}$/Mg$^{+2}$-free). Cells were scraped into lysis buffer (20 mM Tris-HCl, pH 7.4, 1mMEDTA 1 mM phenylmethyl sulfonyl fluoride (PMSF), 10 $\mu$/ml aprotinin and 1 mM leupeptin). Cells were lysed by several rounds of freezing (–70° C.) and thawing (37° C.), and clarified by centrifugation at 15,000×g at 4° C. for 1 h. To obtain nuclei, lysis buffer was made 25 mM sucrose and 150 mM sodium chloride prior to freezing and thawing. Nuclei were isolated following a 600×g centrifugation at 4° C. for 5 min. Nuclear homogenates were obtained by resuspending nuclei in lysis buffer in the presence of 1 $\mu$/ml of deoxyribonuclease and 150 mM sodium chloride, and incubating samples on ice for 30 min. Nuclear debris was removed by centrifugation at 15,000×g for 30 min. Supernatants containing approximately 100 $\mu$g of protein or an equal number of counts per minute from membrane particulate, nuclei and cytoplasm were transferred to tubes containing 2 $\mu$g of anti-c-myb (Genosys; Woodlands, Tex.), anti-PKC a $\alpha\beta\gamma$ and PKCE immunoglobulins (IgG), (Gibco BRL; Gaithersburg, Md.) or nonimmune IgG and incubated at 4° C. for 16 h with mixing. Protein A sepharose was added and lysates incubated for an additional 1 h. Precipitates were washed six times in lysis buffer containing 0.15M sodium chloride and fractionated through a 10% polyacrylamide gel in the presence of sodium dodecylsulfate (SDS-PAGE), and western blotted as previously described. Gadson, P. F. et al. (1996), Differential response of mesoderm and neural crest derived smooth muscle to TGF-$\beta$1: regulation of c-myb and $\alpha$1 (I) procollagen genes. *Exp. Cell. Res.* (in press).

.sn-1,2-Diacylglycerol assay: VSMC were treated with 0.01 to 100 $\mu$M H[cys] for 15–60 min. Cells were harvested and lipids were extracted by the method of Priess et al., (18). The analysis of diacylglycerol synthesis was as described previously by Wrenn et al. Wrenn, R. W. et al. (1993). Transforming growth factor-Beta: signal transduction via protein kinase C in cultured embryonic vascular smooth muscle cells. *In Vitro Cell. Dev. Biol.* 29A:73–78.

Protein kinase C activity: Protein kinase C activity was determined using a method of a previously published procedure with modifications. Wrenn, R.W. et al. (supra). Briefly, harvested VSMC were fractionated by resuspending cell pellets in 20 mM Tris/pH 7.5 containing 1 mM EDTA, 16M NaCl, 1 mM PMSF, 0.15 $\mu$M aprotinin and 0.25 M sucrose (TEPA buffer with sucrose) and subjected to several rounds of freezing (–70° C.) and thawing (37° C.) until the supernatant was cloudy. Nuclei were isolated by centrifugation at 600×g for five min. and particulate membrane and cytosol fractions were isolated from homogenate by ultracentrifugation at 100,000×g for one hour. Nuclei were resuspended in HEPA buffer and treated with 1 unit of deoxyribonuclease at 4° C. for 10 min. Nuclear homogenates were sonicated and extracts subjected to centrifugation at 15,000×g for 30 min. Each of these fractions was analyzed for total PKC activity in the presence and absence of calcium chloride as described previously. Wrenn, R. W. et al. (supra). Calcium was not required for the activation of 90% of the nuclear bound PKC. Furthermore, calcium concentrations above lmM and higher inhibited nuclear and 30% of the particulate membrane PKC activity.

Figure 2A:
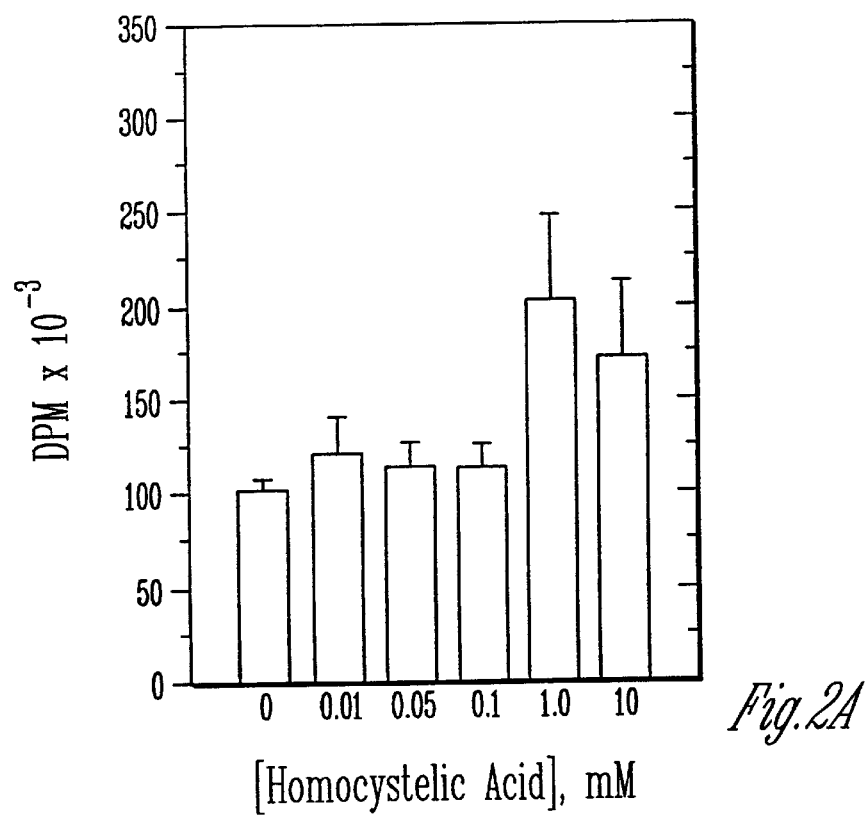
FIGS. 2A–2C are graphs illustrating the effects of glutamate, homocysteic acid and NMDA on DNA synthesis in N-VSMC. N-VSMC were cultured and serum-deprived as described in "Experimental Procedures." Cultures were treated with various concentrations of homocysteic acid (2A), NMDA (2B), or L-glutamate (2C) for 30 and pulsed 6h with [$^3$H] thymidine. All values are expressed as ±S.D. of six independent experiments completed in quadruplicate.
Figure 2B:
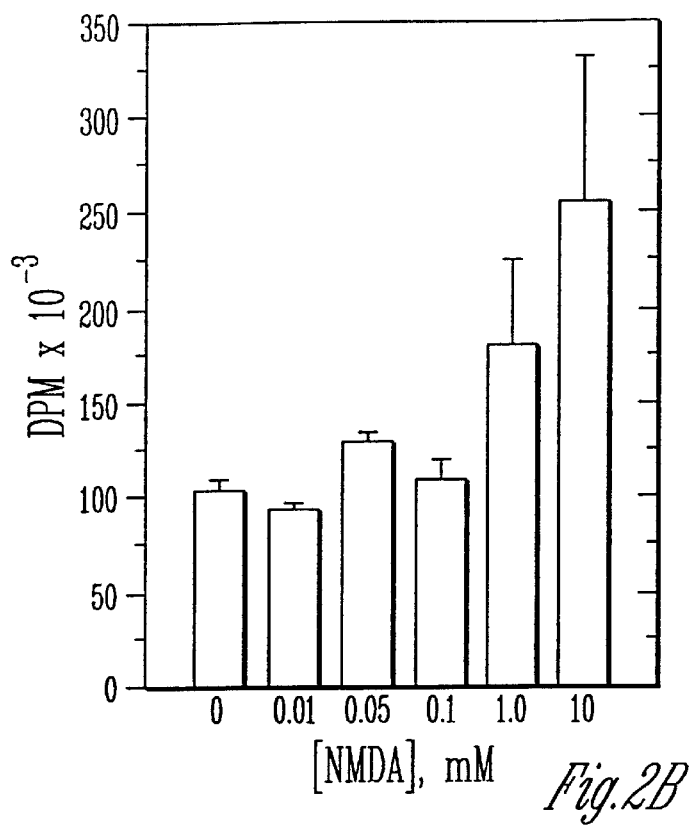
Figure 2C:
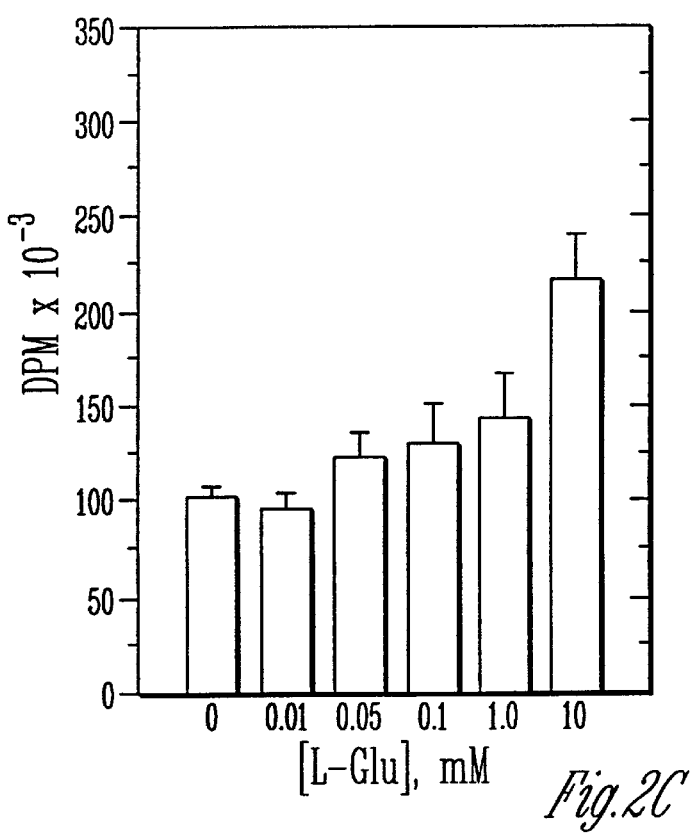

Effect of homocysteine on DNA synthesis, and cell proliferation. When N-VSMC were incubated with 0.01 to 4000 $\mu$M homocysteine, DNA synthesis was increased 12-fold in a dose dependent and saturable manner (FIG. 1). The effect of homocysteine on DNA synthesis was observed with different isolates of N-VSMC; and the effect was observed with human cell cultures of N-VSMC (data not shown). However, VSMC isolated from abdominal (N-VSMC) did not respond similarly (FIG. 1). To determine the specificity of the homocysteine response, cell cultures were incubated with various concentrations of glutamate, N-methyl D-aspartate acid (NMDA) and homocysteic acid. The data in FIG. 2 shows that 1 mM homocysteic acid, 10 mM glutamate and NMDA stimulated [$^3$H] thymidine incorporation 2-fold in N-VSMC. These concentrations were 10 to 50-fold higher than 0.1 mM homocysteine, suggesting that the response was specific for non-glutamate receptor binding of transport proteins.

Figure 3C:
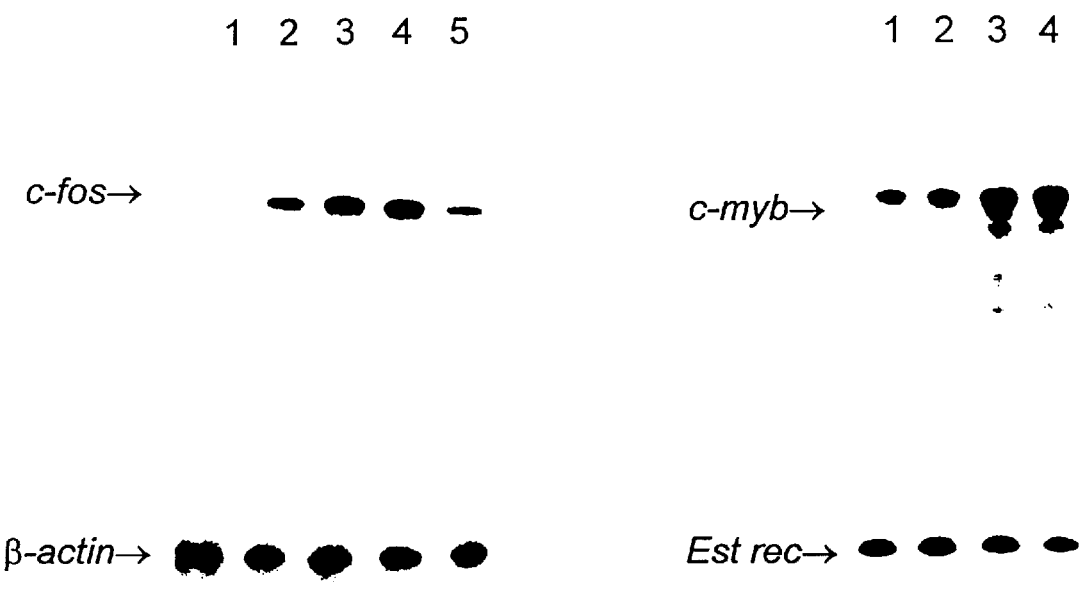
Figure 3C:
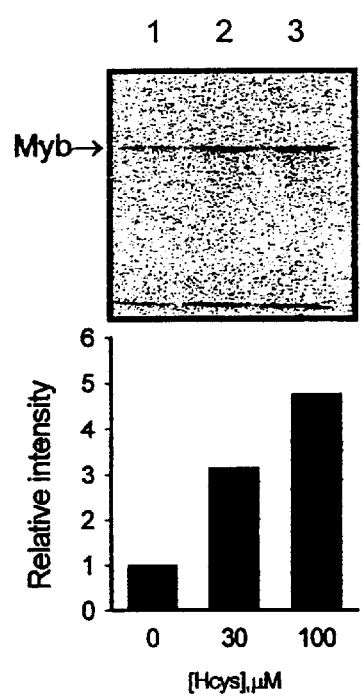
Figure 4:
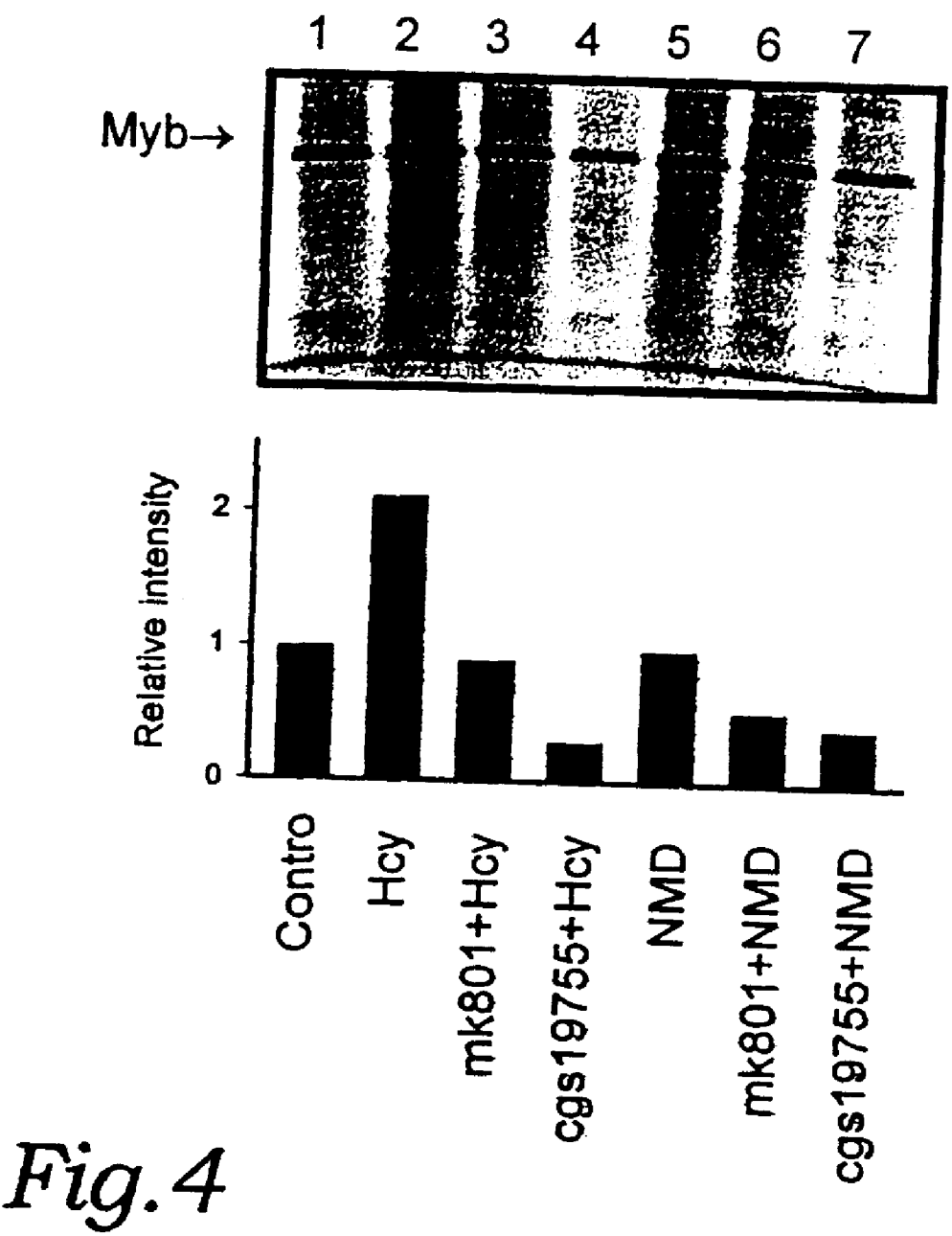
FIG. 4 is a graph illustrating the analysis of c-myb synthesis in response to NMDA receptor antagonist, Mk-801 and CGS19755. Immunoprecipitation and western blotting of radiolabeled c-Myb from N-VSMC treated with 200$\mu$MH [cys] in the presence and absence of 50 $\mu$M Mk-801 or 1 mM CGS19755. Cell cultures were treated with and without H[cys] for 24 hours, extracts were immunoprecipitated with anti c-myb IgG and samples were separated by SDS-PAGE gels and western blotted. The amount of specific radiolabeling in the autoradiograph was quantified by scanning densitometry. The size of the c-Myb protein is 75 kilodaltons. The 75 kilodalton band is defined as c-Myb because immunoprecipitation of this protein was not detected in the presence of synthetic polypeptide [I13-Gln-Arg-His-Tyr-Asp-Glu-Asp-Pro-Glu-Lys-Glu-Arg-Ile-Lys-Glu-Leu; encoded by sequences 1080–1133].

Recently, it was demonstrated that the growth of N-VSMC was blocked by c-myb antisense oligodeoxynucleotides. As shown in FIG. 3, c-myb and c-fos MRNA transcripts were induced 6 to 15-fold in response to 200 $\mu$M homocysteine treatment, respectively. To further evaluate the mediator(s) of the homocysteine response and the relationship to a glutamate receptor of transporter, non-competitive and competitive blockers of NMDA type glutamate receptor were used, and the effect of these inhibitors on c-myb expression determined. When cells were treated with homocysteine and CGS 19755, a competitive inhibitor of NMDA receptor ligand binding site, c-myb induction was blocked and no increase in cell proliferation was observed (data not shown). Moreover, Mk-801, a non-competitive inhibitor of the NMDA receptor calcium channel, completely suppressed the homocysteine effect on c-myb induction (FIG. 4.).

Figure 5A:
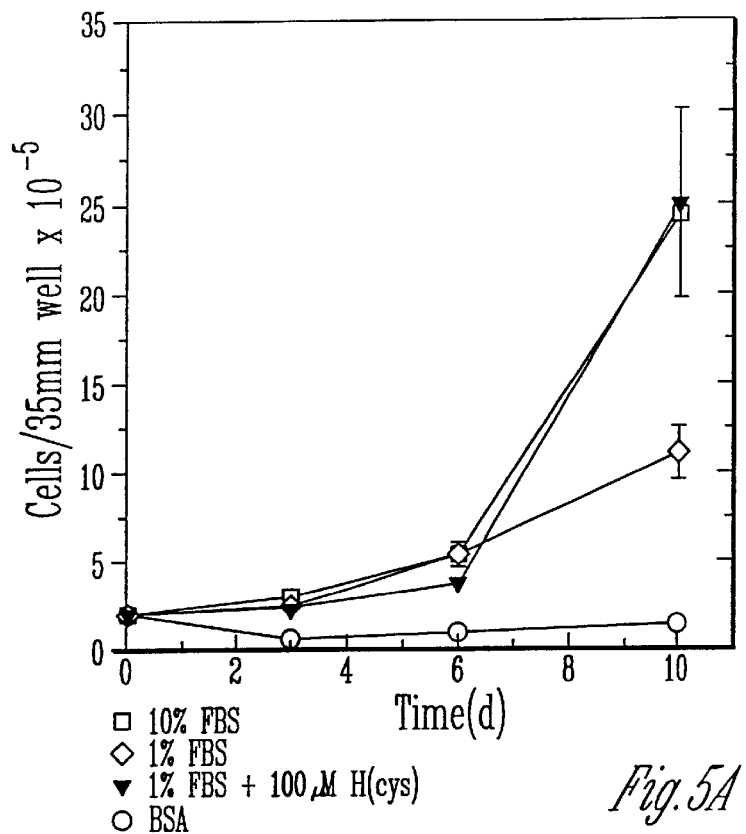
FIGS. 5A and 5B are graphs illustrating cell growth and DNA synthesis of N-VSMC cultures. (A) Cells were cultured in M199 supplemented with 1% FBS in the presence and absence of 100 $\mu$M H[cys]. The medium was renewed every three days and cell numbers were determined by Coulter counter or emocytometer. Each point represents the mean of quadruplicate samples counted six times. (B) Cells were grown to confluency, growth arrested in M199 and 1 $\mu$g/ml of bovine serum albumin for two days. Cultures were exposed to various concentrations of H[cys] (0.01–1000 $\mu$M) for 30 h, pulse labeled for 6 h with 2 $\mu$Ci/ml of [$^3$H]thymidine. The amount of [$^3$H]thymidine incorporation was determined by scintillation spectrophotometry. Results are shown as the mean of ±S.E.M.
Figure 5B:
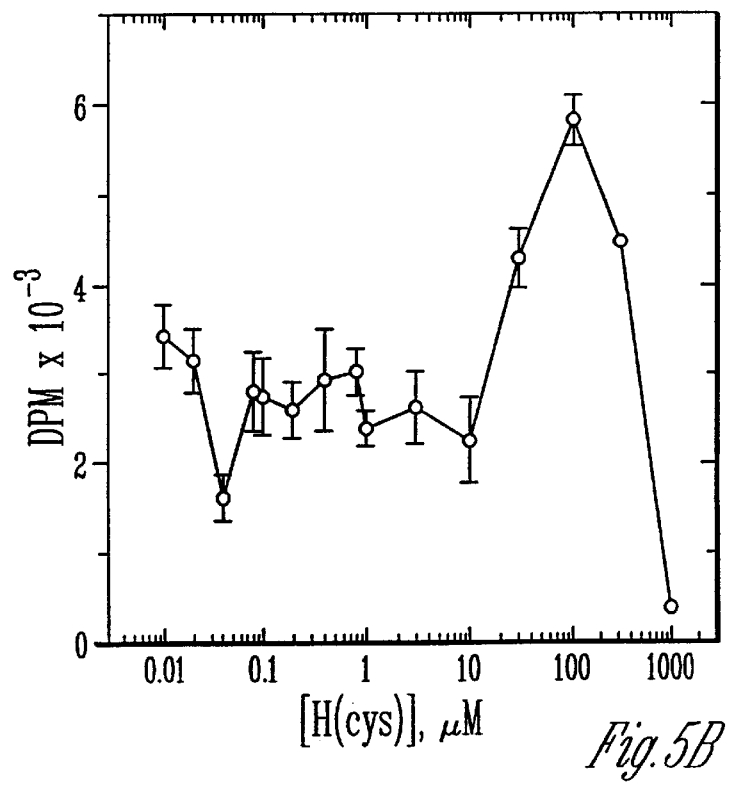

Further studies were undertaken to elucidate whether the homocysteine effects on c-fos and c-myb expression and DNA synthesis would stimulate cell proliferation. N-VSMC were grown for several days in the presence and absence of homocysteine and, as shown in FIG. 5A, homocysteine increased cell number 9-fold between day 6 and 10 in the presence of 1% serum. The apparent increase in the rate of cell proliferation by homocysteine was similar to that observed in 10% fetal bovine serum. This data is very similar to experiments reported by Tsai et al. Tsai, J-C et al. (1994). Promotion of vascular smooth muscle cell growth by homocysteine: A link to atherosclerosis, *Proc. Natl. Acad. Sci.*, 91:6369–6373. Their data also showed that homocysteine is a potent stimulant of cell proliferation in the presence of low levels of serum. However, VSMC incubated for six days and treated with 0.01 to 100 $\mu$M for 36 h were able to incorporate [$^3$H] thymidine in the absence of serum, but no increase in cell number was observed (FIG. 5B). Furthermore, homocysteine concentrations above 300 $\mu$M completely suppressed DNA synthesis. This data suggests that H[cys] can stimulate in VSMC, however, a component in the serum is needed before cells are able to complete mitosis.

Figure 6A:
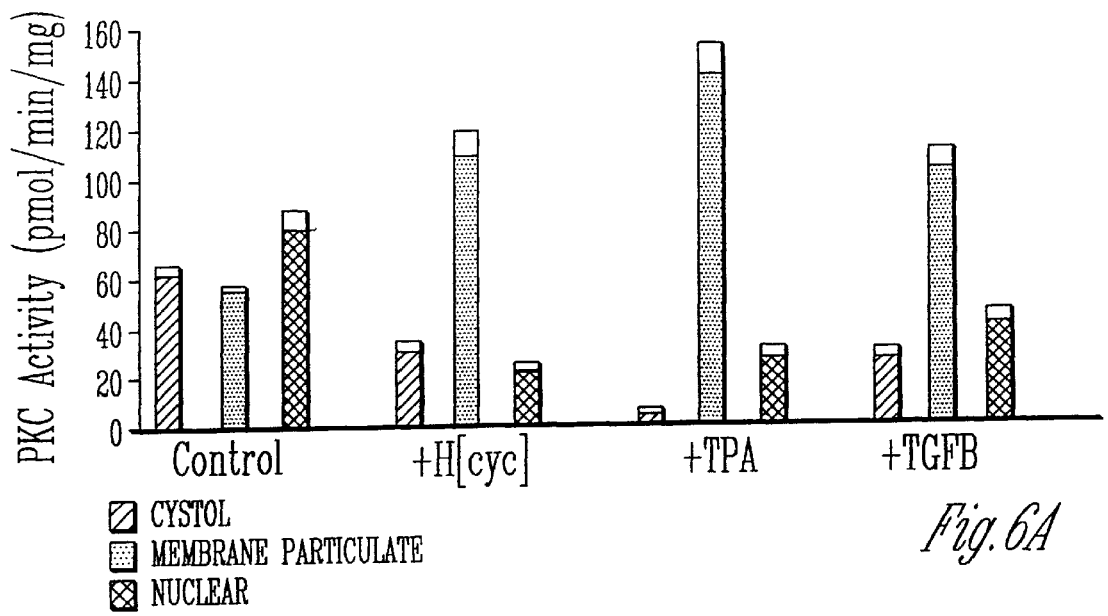
FIGS. 6A–6C show the distribution of protein kinase C in the presence of H[cys], TPA and TGF $\beta$1. (A) Cell cultures were treated without reagents or with 200$\mu$M H[cys] or 2 ng/ml TGFB1 for 1 h, or with 5 nM TPA for 30 min prior to cell fractionation. Cells were harvested and separated into cytosol membrane particulate and nuclear fractions, and PKC activity measured as described in Material and Methods. The data are reported as the mean ± standard error of eight separate determinations. (B) Immunolocalization of PKC epsilon in M- and N-VSMC. Cell cultures were plated and grown for three days prior to immunohistochemistry staining of PKC epsilon in the N-VSM (bottom) contrasted with the low levels of expression of the enzyme in M-VSMC (top). The staining can be seen in cytosol, nucleus and associated with intracellular fibers. (C) Use of PKC epsilon IgG to detect enzyme in M- and N-VSMC by western blot. The C-lane represents purified recombinant PKC epsilon; M and N are samples derived from mesoderm (abdominal ) and neurocrest & (thoracic) smooth muscle cells, respectively.
Figure 6B:
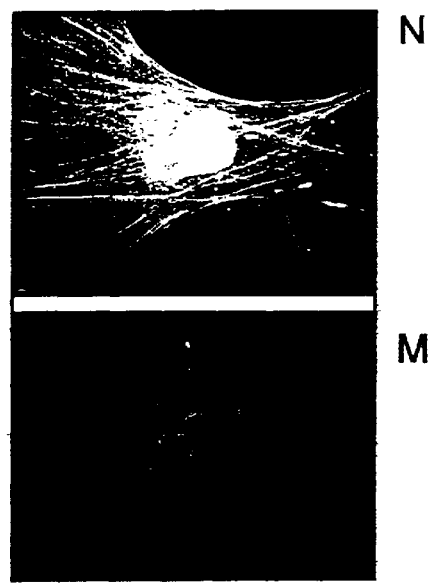
Figure 6C:
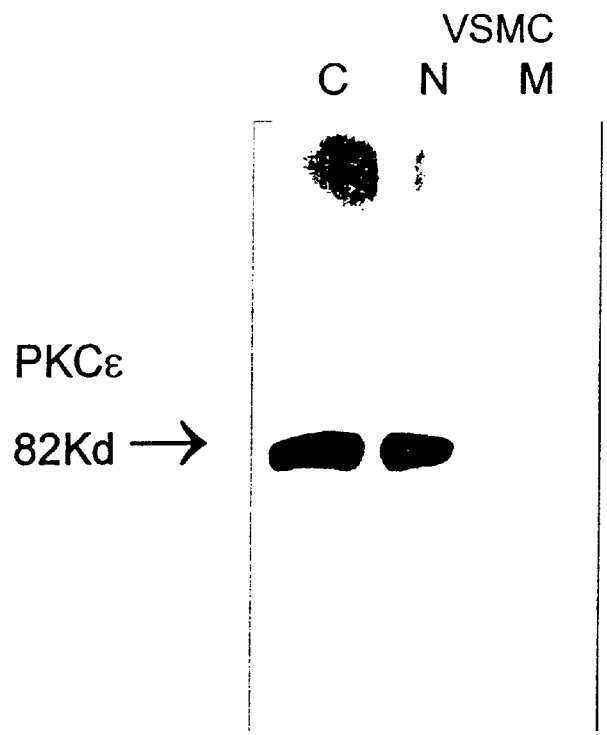

The role PKC in the H[cys] effect on cell proliferation. Since the mechanism of action of homocysteine was unknown, the present inventors studied the intracellular signaling events that accompanied homocysteine treatment of smooth muscle cells. Diacylglycerol and protein kinase C are among the catalysts that have been examined most extensively in vascular smooth muscle. Protein kinase C was found to be equally distributed among the membrane particulate, nuclear and cytosol fractions in untreated N-VSMC (FIG. 6A). Treatment of N-VSMC with 100 $\mu$M H[cys] for 60 min. resulted in a significant increase in membrane-associated PKC combined with a loss of enzyme activity in the cytosolic and nuclear fractions. TGFP and tetradecanoyl phorbol 13-acetate (TPA), two other agents that alter the distribution of PKC activity, demonstrated similar responses (FIG. 6A). The nuclear bound PKC activity appeared to be the epsilon isoform since more than 90% of the enzyme activity could be precipitated with a PKC epsilon monoclonal (data not shown). M and N-VSMC were analyzed for the expression of the different PKC enzymes and, as demonstrated by immunohistochemistry and western blot analyses in FIG. 6B and C, N-VSMC expressed at least 50-fold higher levels of PKC epsilon that M-VSMC. The other PKC isoforms were expressed at similar levels in both cell types (data not shown). Thus, the difference in response to H[cys] between the Mand N-VSMC may be due to the levels of PKC epsilon.

Figure 7A:
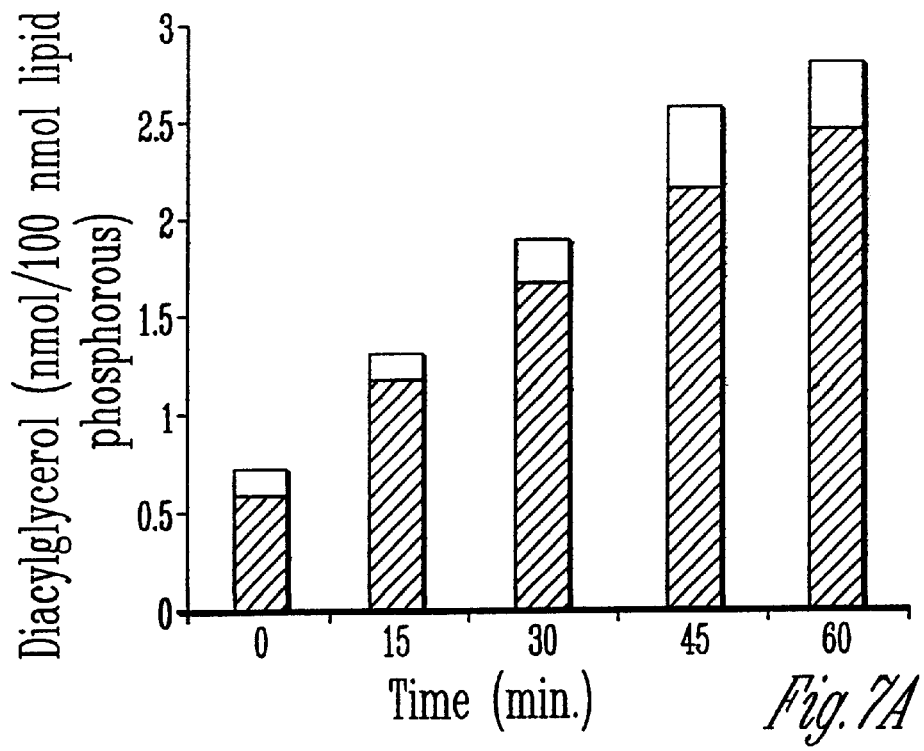
FIGS. 7A–7C are graphs illustrating the effect of H[cys] on diacylglycerol content in N-VSMC. (A) Time course of changes of membrane diacylglycerol content cell treated with 100$\mu$M H[cys] for the various times. Cells were recovered, membrane lipids extracted and diacylglycerol amounts determined as described in Methods. Results are expressed as the mean ± standard error of quadruplicate incubations from six independent experiments. (B) Effects of varying concentrations of H[cys] on diacylglycerol synthesis. Cells were treated for 30 min with different concentrations of H[cys] and membrane lipids were isolated and the diacylglycerol content determined. (C) Effect of PKC inhibitors on H[cys] mediated cell proliferation. N-VSMC cultures were grown in 1% FBS and 100 µM H[cys] in the presence and absence of staurosporine and cheleyrithrine chloride for the times (days-d) indicated. Cells were counted in quadruplicate in a Coulter counter every three days. Values represent the mean ±S.D. from four independent experiments.
Figure 7B:
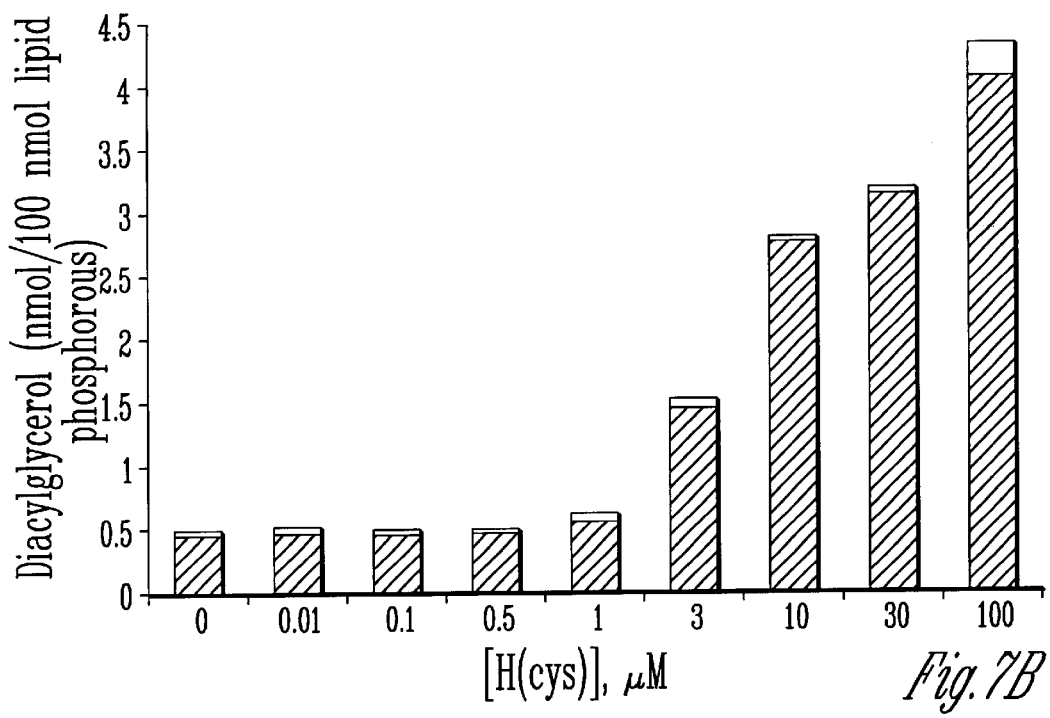

To further examine the interaction of H[cys] with the PKC system in VSMC, the effect of H[cys] on diacylglycerol (DAG) synthesis was measured. VSMC cultures treated for 15–60 min. with H[cys] resulted in a 3-fold increase in DAG production (FIG. 7A). The concentration curve for DAG production in VSMC is shown in FIG. 7B. The increase in DAG membrane levels in VSMC was first evident in 3 $\mu$M H[cys] and was elevated significantly in 100 $\mu$M H[cys]. The increase in membrane-associated DAG preceded the translocation of PKC activity. These results are consistent with the role of DAG as an activator of all PKC enzymes. The activation of many neurotransmitter receptors have been shown to increase DAG, and are coupled to phospholipase C, which hydrolyzes phosphoinositides to DAG. The phospholipase responsible for the production of DAG in response to H[cys] is unknown; however, the receptor for metabotropic excitatory amino acids and a subclass that is specific for sulfur containing amino acids, such as L-cysteine sulfinic, is coupled to phospholipase D. The activation of receptors coupled to phospholipase D catabolize the metabolism of phosphatidylcholine, which could produce much more DAG than receptors coupled to phospholipase C- phosphoinositide hydrolysis, because phosphatidylcholine is a major component of the plasma membrane.

Figure 7C:
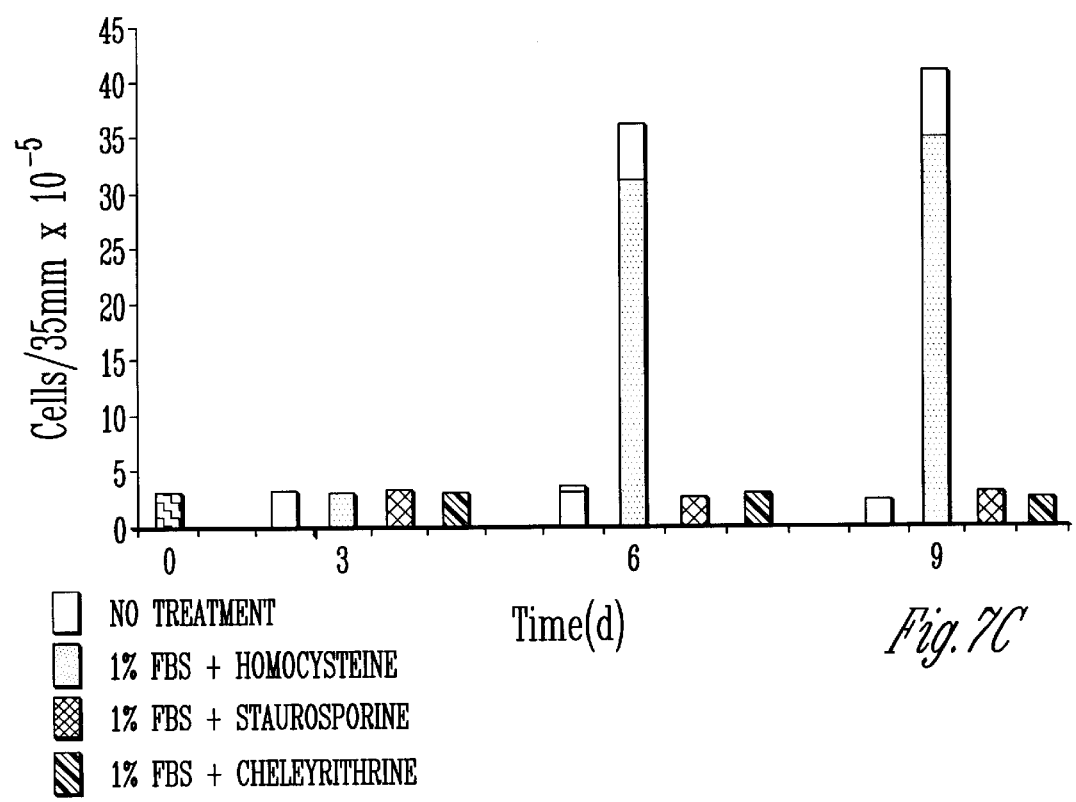

The potential relationship between cell proliferation and PKC activation in response to H[cys] in N-VSMC was examined in experiments measuring cell number in the presence and absence of PKC inhibitors, staurosporine and cheleyrthrine chloride. As shown in FIG. 7C, both inhibitors of PKC activity blocked the increase in cell number observed in the presence of H[cys]. This data also demonstrated that treatment of VSMC for ten days with low levels of PKC inhibitors did not permanently damage the cells, because they could be stimulated to grow after the removal of both staurosporine and cheleyrithrine chloride (data not shown).

The recent work by Tsai et al. (supra) did not link H[cys] to a signal transduction cascade; however, their report is consistent with the results of the present study. The concentrations of H[cys] that elicit the growth response in our study correlate well with the amounts of homocysteine present in patients with homocystinuria. Previous reports suggested that the mental retardation associated with homocystinuria patients might be caused by the over-stimulation of NMDA receptors. However, the investigators were unable to detect the conversion of H[cys] to homocysteic acid and homocysteinesulfinic acid, two potent agonists of NMDA receptors. The above data demonstrates that there are receptors for H[cys], either intracellular or associated with the plasma membrane that are stimulated by homocysteine, and coupled to phospholipase activity and diacylglycerol production. Svardal et al. measured the subcellular distribution of H[cys] binding in rat liver cells and determined that 50% of protein bound H[cys] appeared in the microsomal fraction, 30% in the cytosol fraction and 20% of the bound H[cys] was associated with membrane particulate. Svardal, A. et al. (1986). Determination of in vivo protein binding of homocysteine and its relation to free homocysteine in the liver and other tissues. *J. Biol. Chem.* 261:3156–3163. The H[cys] binding proteins that mediate the growth response observed in VSMC are probably related to NMDA receptors in the ligand binding domain and the calcium ion binding site. Mk-801 and CGS19755, inhibitors of the NMDA receptor calcium and ligand binding sites, block the H[cys] effect on the induction of c-myb and cell proliferation, which suggest a similar ion and amino acid requirement for activation of the H[cys] binding protein.

The finding that L-glutamate and NMDA do not significantly activate the same responses as H[cys], but NMDA receptor antagonist inhibit H[cys] mediated events, suggest that the specificity for H[cys] binding is due to the presence of the sulfhydryl group. Amino acids like H[cys] may be part of a signal transduction cascade in which changes in redox state activate membrane receptors. Recent studies suggest that tyrosine kinase receptors located in the endoplasmic reticulum can be activated by changes in redox potential. Bauskin, A. R. et al. (1991). Redox regulation of a protein tyrosine kinase in the endoplasmic reticulum. *Cell* 66:685–696.

Moreover, the above data also implies that the specificity of the clinical manifestations associated with homocystinuria patients is due to the expression of H[cys] binding proteins in cells of the affected tissues and organs.

Based on the above responses to Hcy, the magnitude of the responses, and their rapid time of onset, the inventors inferred that the responses must be receptor-mediated, and that there must be a receptor for Hcy on the plasma membrane of the aortic smooth muscle that was signaling the growth responses. There is no description in the literature of a specific receptor for the growth factor effects of Hcy. However, Hcy has been reported to be a weak agonist of N-methyl-D-aspartate (NMDA) receptors in the central nervous system, and NMDA receptors are known to have an important growth effect for developing neurons. Thus, the inventors postulated that the growth factor effects of Hcy could occur as a result of Hcy interacting with a member of the NMDA receptor family. Radioligand binding showed that two selective NMDA receptors were bound to aortic smooth muscle cell membranes with 20–25% specific binding.

EXAMPLE 2

Blocking the Growth Factor Effects of Hcy

C-Myb

In accordance with the experimental procedures of Example 1, embryonic smooth muscle cells were treated with isoleucine control, with 200 $\mu$M Hcy, or with 200 $\mu$M Hcy and NMDA receptor antagonists. Hcy-induced expression of Myb was inhibited by both competitive and non-competitive NMDA receptor antagonists. NMDA per se did not induce expression of Myb. This data further implies that there is a unique receptor for Hcy that is related to the NMDA receptor family. The results are shown in FIGS. 9A and 9B. Further evidence for the relationship between the Hcy receptor and the NMDA receptor family is given below.

Uptake of Tritiated Thymidine

First or second passage smooth muscle were treated with 100 $\mu$M Hcy or isoleucine as described above. Alternate cultures were treated with competitive and non-competitive NMDA receptor antagonists, and tritiated thymidine uptake was measured. The uptake of tritiated thymidine was inhibited by NMDA receptor antagonists, as set forth in FIGS. 9A and 9B.

EXAMPLE 3

Signal Transduction

In order to obtain a response that could be used for rapid throughput evaluation of the effects of a variety of NMDA antagonists, the inventors looked into calcium flux.

Calcium Signaling

Figure 8A:
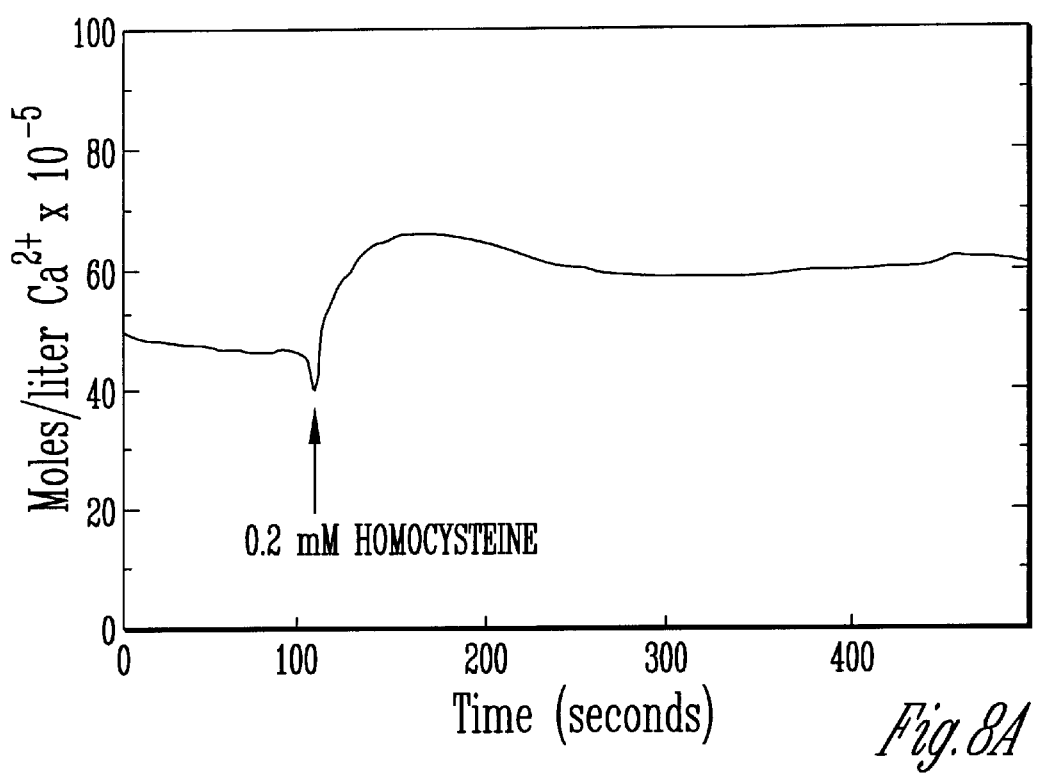
FIGS. 8A and 8B are graphs illustrating E14 embryonic neural crest-derived response to Hcy. (A) Normal E14 cell response; (B) Ca++ influx is prevented by 15 min pretreatment with NMDA receptor blocker MK801, which acts at the NMDA receptor calcium channel.
Figure 8B:
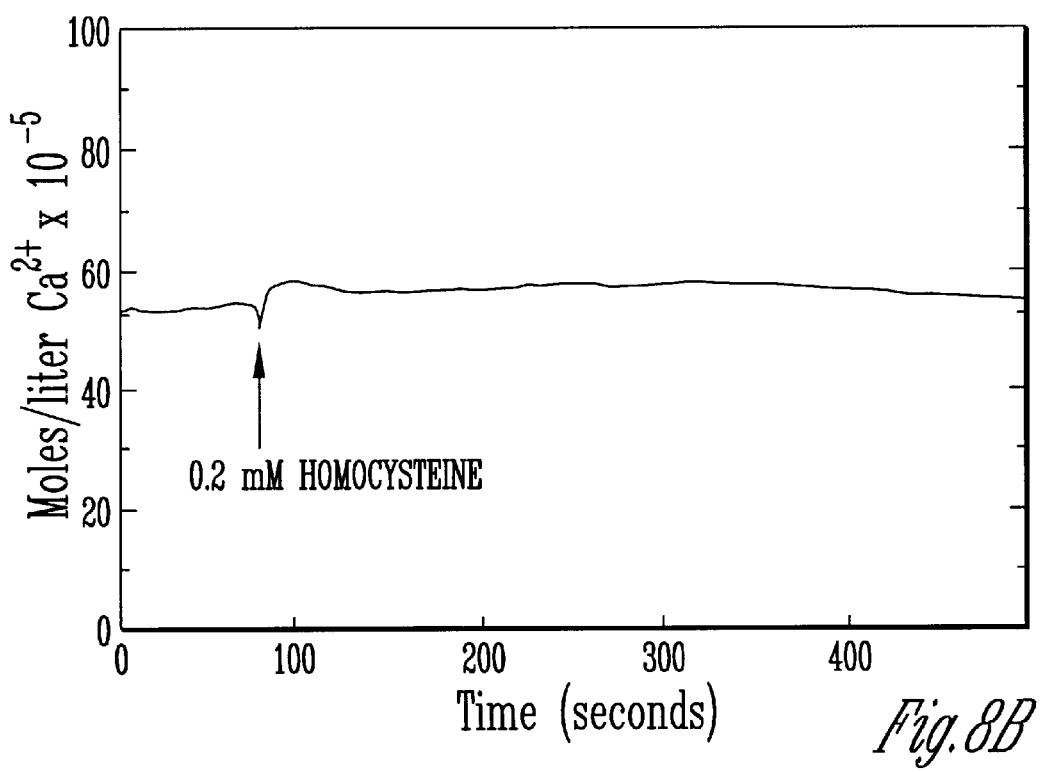

The most common signaling device for mitosis is calcium influx. Therefore, the inventors measured the change in intracellular $Ca^{++}$ by Fura 2 fluorometry. Thoracic aorta VSMC from E14 embryos were harvested and grown on coverslips using the procedure set forth above. Fura 2 was added during 45 minutes at room temperature. Then the cover slips were placed in a photometer. Fura 2 was excited at 350 and 380 nm with a xenon light source, appropriate monochromators and a chopper (Deltascan, Princeton). Emitted signals passed through a 510±20 band pass filter. When the cells were treated with a solution of 200 $\mu$M Hcy, there was a rapid flux of $Ca^{++}$ that reached a plateau in about 50 seconds, and remained elevated for the duration of the 500 sec measurement interval as shown in FIGS. 8A and 8B. Similar results have been found with adult rabbit aortic smooth muscle cells, as set forth below.

The inference that Hcy may be a growth factor for smooth muscle cells was extrapolated to the hypothesis that Hcy may be part of the array of factors that interact during the process of atherogenesis, with a particular impact upon smooth muscle cells. This hypothesis is supported by reports that hyperhomocystinemia in man induces growth of the intima-media of carotid artery; and the atheroma that accompanies homocystinuria in man is composed principally of smooth muscle cells and matrix, with little or no lipid deposition.

Since Hcy had a significant mitogenic effect on embryonic avian smooth muscle cells, as well as those from adult human aorta (see below), the next step was to extend the studies to an animal model of atherosclerosis. The recent development of murine models of atherosclerosis (both dietary and genetic) presents several advantages, both practical and scientific, including the rapid development of advanced lesions in as little as 15 weeks in the apolipoprotein (apo) E-deficient mouse. Furthermore, atherosclerosis cystathione-beta-synthase (CBS) knockout mouse also is available, yielding atherosclerosis model of severe hyperhomocystinemia in the homozygote and moderate hyperhomocystinemia in the heterozygote. Other strains of mouse have shown susceptibility to atherosclerosis when they were placed on high-fat diets. These several models appeared to make available a number of attractive possibilities upon which the theory could be tested, for example, giving apoE-deficient mice atherosclerosis high methionine diet, giving CBS knockout mice a high fat diet, or feeding a susceptible strain a diet that was simultaneously high in fat and high in methionine. In preparation for further studies, it was necessary to define the effect of Hcy upon murine smooth muscle cells in vitro.

EXAMPLE 4

Effect of Homocysteine on Mouse Vascular Smooth Muscle Cells

The mitogenic and other effects of growth factors are exaggerated in late embryonic or fetal smooth muscle cells, and cells in the late fetal state provide a high contrast picture of their subsequent, post-natal, responses. To take advantage of this effect, late fetal C57BL/6×129 mice were obtained and aortic smooth muscle cell cultures were prepared according to the inventors' previously published methods set forth above. These cells were treated with a series of Hcy dilutions (10 $\mu$M–100 $\mu$M) as described above. There was no enhancement of $^3$H thymidine uptake, and no mitosis that resulted from the Hcy treatment. Subsequently, the fetal mouse smooth muscle cells were treated with a number of variations of the incubation medium containing the Hcy. In no case did Hcy produce a measurable mitogenic effect.

Figure 9:
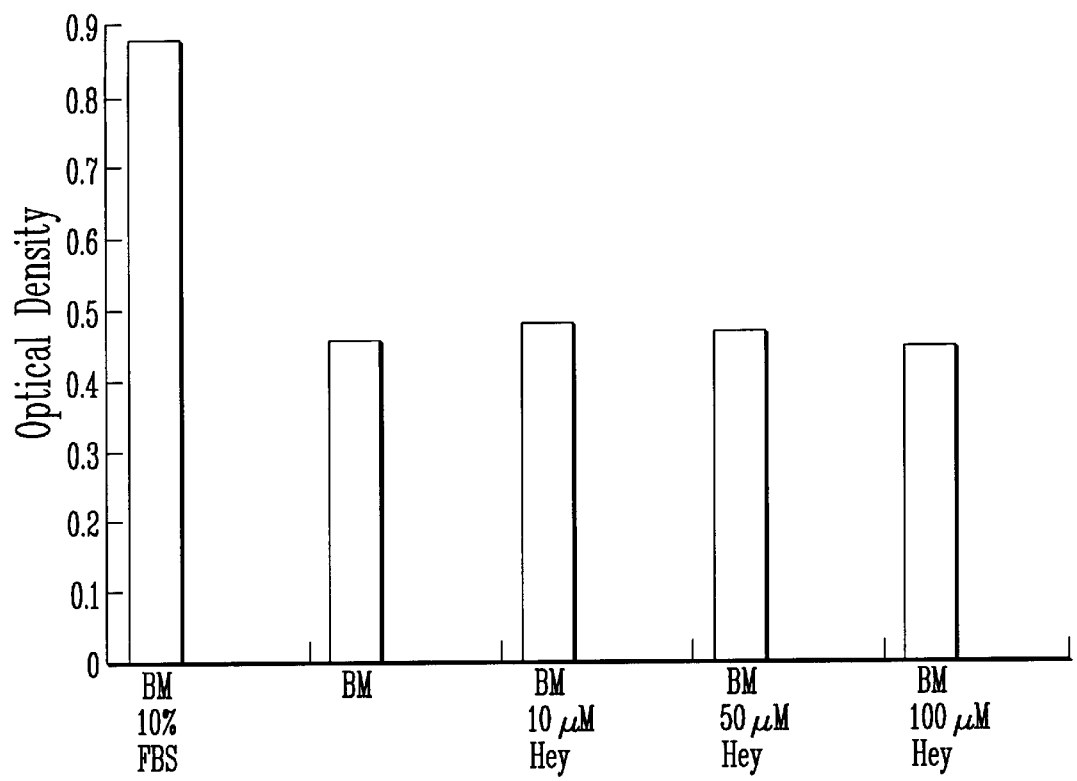
FIG. 9 is a bar graph illustrating the results of treatment of mouse aortic smooth muscle cells with various concentrations of Hcy. No mitogenic result was shown.

To determine if this result was persistent, adult C57Bl/6 mice with a known susceptibility to diet-induced atherosclerosis were obtained. Aortic smooth muscle cells were obtained from mice of this strain that were 3–6 months old, and were treated with various concentrations of Hcy. Again, there was no mitogenic effect, as shown in FIG. 9.

Hcy had no effect on mouse aortic smooth muscle cells in vitro. The inventors concluded that hyperhomocystinemia would probably not effect the origin or progression of atherosclerosis in the mouse in vitro, and that the mouse would be an inappropriate model to study the atherogenic effects of Hcy. Preliminary data obtained by others support this hypothesis: in the homozygous cystathione-β-synthase deficient (CBS-1) mouse, extreme elevation of serum Hcy levels of several months duration does not produce any atherosclerosis (Nobuyo Maeda, personal communication); the mice die of liver disease, whereas in man there is no significant liver disease in patients with homocystinuria, and they typically die from thromboembolic complications of precocious atherosclerosis. Furthermore, in the heterozygous CBS+/-mouse, moderate hyperhomocystinemia does not appear to accelerate the progress of atherosclerosis of hyperlipidemic origin (Maeda, personal communication). Subsequent to the finding that the mouse model was inappropriate for evaluation of the role of Hcy in atherogenesis, the rabbit model was selected.

EXAMPLE 5

The Effect of Homocysteine on Rabbit Vascular Smooth Muscle Cells

For each of the following experiments, aortic smooth muscle cells were obtained from 2–3 lb. New Zealand rabbits; these cells were cultured as described above, and evaluated for their responses to Hcy.

Calcium Uptake

Figure 10:
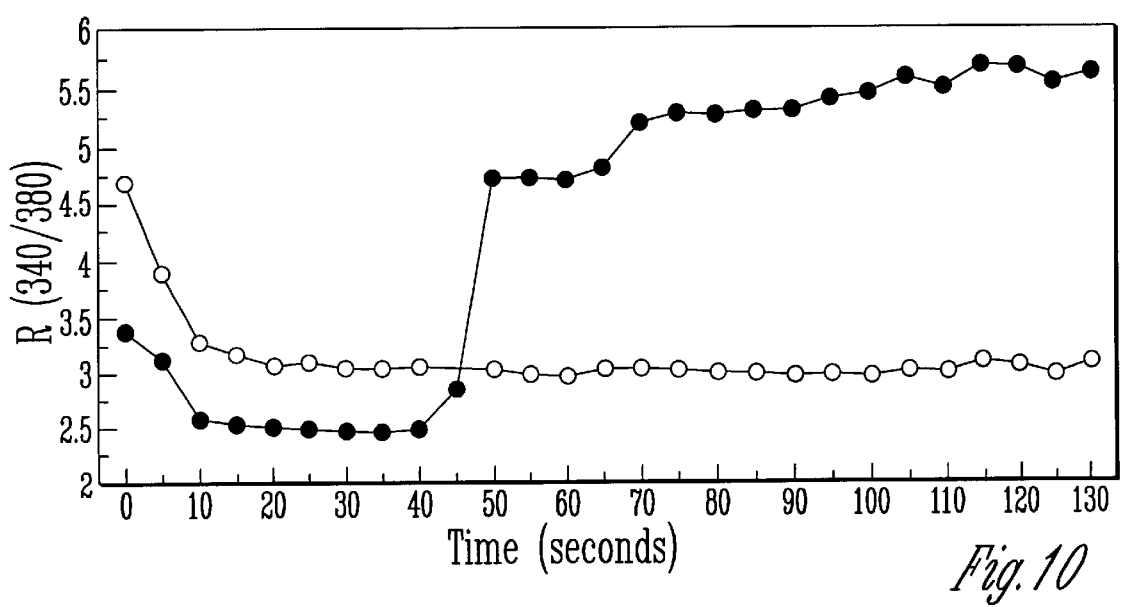
FIG. 10 is a graph illustrating the results of treatment of rabbit aortic smooth muscle cells with various concentrations of Hcy.

Rabbit aortic smooth muscle cells treated with $10 \mu M$ Hcy for 40 seconds showed a significant calcium flux that was maintained for the duration of the 130 second measurement interval, as shown in FIG. 10. This response is similar to that of the embryonic cells (see above). Although histochemical analysis showed that the cultures contained only smooth muscle cells, they showed a heterogeneous response to Hcy (FIG. 11).

Expression of C-myb

Figure 11:
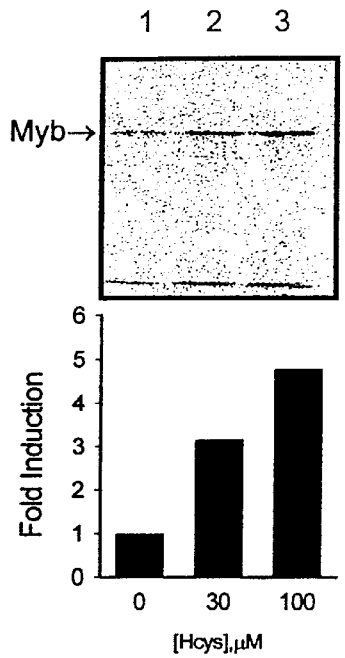
FIG. 11 is a graph illustrating the results of treatment of rabbit aortic smooth muscle cells with Myb protein.

Rabbit aortic cells showed a dose-responsive expression of the Myb protein when they were treated with Hcy (FIG. 11).

Mitogenesis

Figure 12:
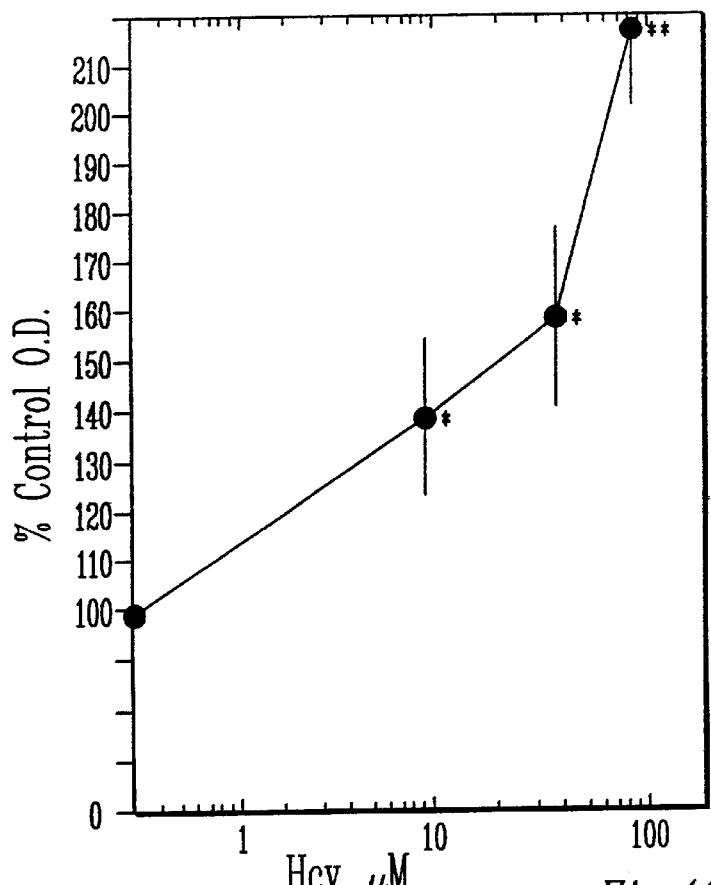
FIG. 12 is a graph illustrating results of treatment of rabbit thoracic aorta smooth muscle cells to differing concentrations of Hcy.

Rabbit aortic cells showed a robust mitogenic response to treatment with Hcy (FIG. 12).

EXAMPLE 6

Effect of Homocysteine on Human Vascular Smooth Muscle Cells

Mitogenic Effect of Hcy: Human Smooth Muscle Cells

Figure 13:
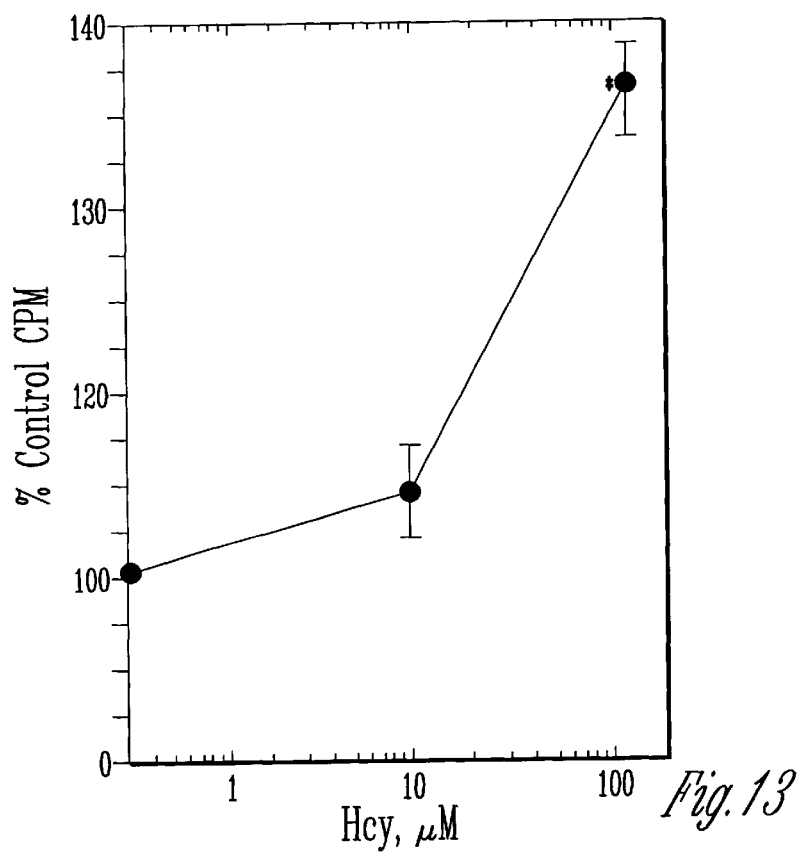
FIG. 13 is a graph illustrating 3 H thymidine uptake of human aortic smooth muscle cells in response to differing concentrations of Hcy.
Figure 14A:
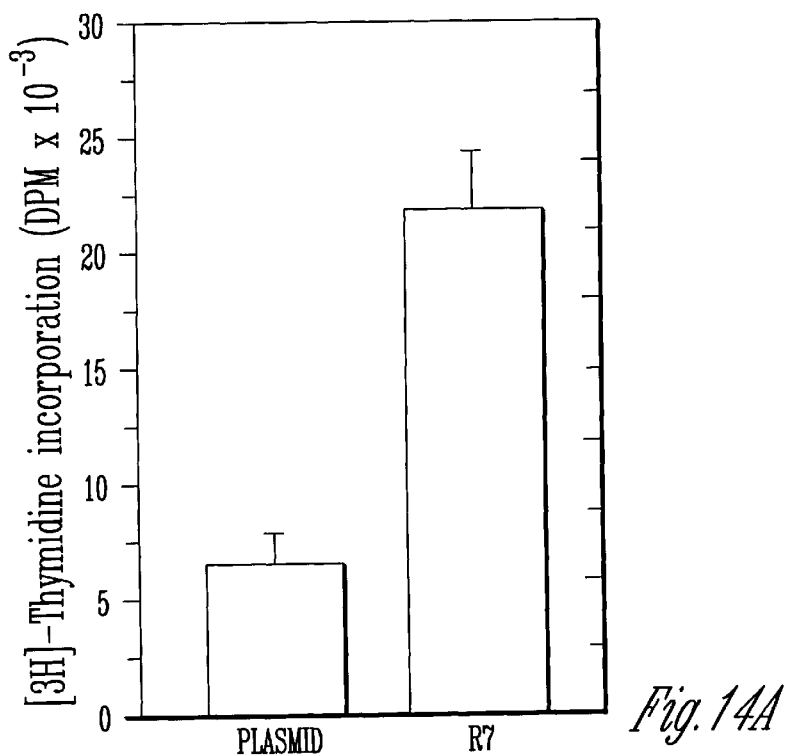
FIGS. 14A and 14B are bar graphs illustrating the effects of [3H]-Thymidine and [35S]-Homocysteine on clone R7. (A) Shows an increase in [3H]-Thymidine incorporation in any cell type transfected with the R7 expression vector. (B) Shows that any cell type transfected with the R7 expression vector has an increase in the binding of [35S]-Homocysteine.
Figure 14B:
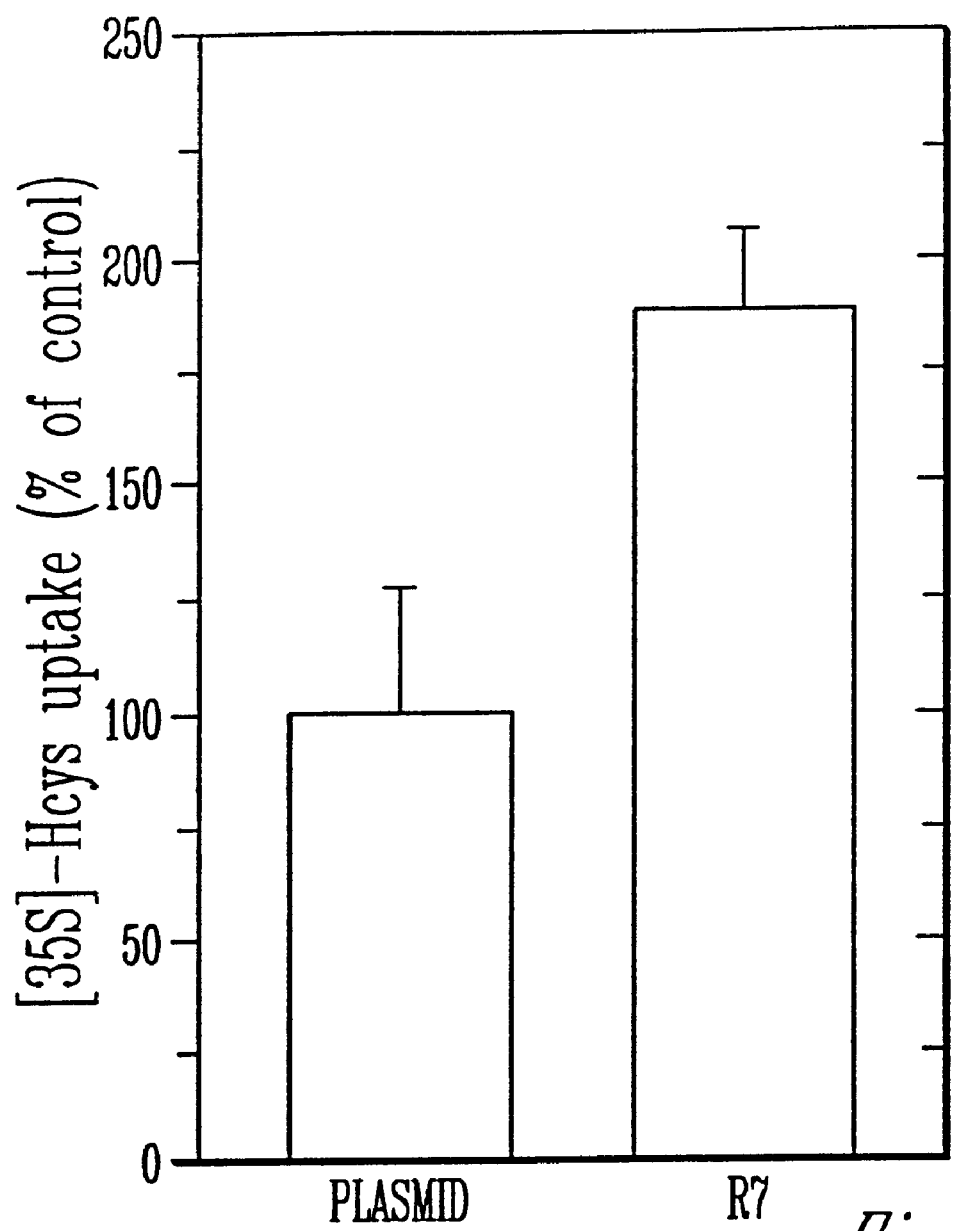

Smooth muscle cell cultures were established from samples of thoracic aorta obtained during organ transplantation. Confluent early passage cells were growth arrested by serum starvation, then they were treated with Hcy in serum free (defined) medium. Hcy treatment produced a significant, dose-responsive increase in uptake of $^3$H thymidine (FIG. 13). This result is consistent with the Hcy concentration-dependent increase in atherosclerosis that has been reported by epidemiologists. This result also is consistent with the finding that high levels of Hcy in humans result in increased wall thickness in the common carotid artery, a neural crest derivative equivalent developmentally to the thoracic aorta; and increased wall thickness of the common carotid correlates highly with plaque formation downstream.

EXAMPLE 7

Hcy Activation of Glutamate Receptors and Stimulation of Calcium Influx

Effect of calcium channel activation on DNA synthesis. Effect of glutamate receptor calcium channels and L-type calcium channels activation was examined by measuring [$^3$H]thymidine labeling. When TA-VSMCs were incubated with NMDA [$^3$H] thymidine was increased 2-fold. DNA synthesis was increased 6-fold when arrested cells were incubated with 0.1 to 1 mM homocysteine. These responses were blocked by Mk801, a non-competitive NMDA receptor antagonist and CGS 19755, a competitive inhibitor of the binding site for glutamate and NMDA. Chelation of extra cellular $Ca^{2+}$ by the addition of EGTA to the medium prevented stimulation of DNA synthesis, suggesting that a transmembrane $Ca^{2+}$ flux caused the proliferative response. Recently, the inventors demonstrated that TGF-β stimulates growth of VSMCs by inducing an autocrine productions and secretion of PDGG-AA. The inventors then decided to determine whether the homocysteine effect on DNA synthesis was due to the autocrine synthesis and secretion of PDGG-AA. The delay in PDGG-AA release from TA-VSMCs in response to TGF-b$_1$ was not observed with cultures treated with 0.2 mM homocysteine. The inventors have demonstrated that c-myb induction is needed for the increases in DNA synthesis in TA-VSMCs. Homocysteine caused a dose-dependent increase in c-myb synthesis, with a maximal effect observed at concentrations of less that 2.5 mM. The homocysteine effect on c-myb expression was blocked by NMDA calcium channel blocker, Mk-801 and by competitive NMDA receptor inhibitor CGS 19755. This data suggests that homocysteine increased c-myb expression after the activation of the NMDA type glutamate receptor. Treatment of cultures with nifedipine, an inhibitor of L-type $Ca^{+2}$ channels, potentiated the homocysteine effect on c-myb expression. Furthermore, nifedipine alone stimulated c-myb expression; and increased DNA synthesis 3-fold in the absence of homocysteine and 10-fold in the presence of homocysteine. Taken together, these findings demonstrate that the effect of the $Ca^{+2}$ influx through the NMDA type of glutamate receptor of TA-VSMCs is antagonized by the L-type $Ca^{+2}$ channel signaling pathway.

The above results demonstrate the following:

1) Homocysteine acts as a mitogenic growth factor for vascular smooth muscle cells, causing increased intracellular $Ca^{++}$ as well as upregulation of jun, fos and myb. These results are consistent with the atherogenic effect of homocysteine.

2) These effects of homocysteine are mediated via a unique homocysteine receptor. Both the pharmacology and the molecular biology show that the homocysteine receptor is a member of the N-methyl-D-aspartate (NMDA) family. As shown by others, ethanol is an NMDA receptor blocker.

3) The pharmacologic effect of homocysteine demonstrated in vascular smooth muscle cells is completely blocked by low concentrations of ethanol, consistent with the low levels that inhibit atherogenesis.

From this data, it can be concluded that drugs in the general family of NMDA receptor blockers are capable of blocking the atherogenic effect of homocysteine. This would constitute a novel application of these drugs. Furthermore, cloning of the receptor will provide knowledge in order to permit the development of new drugs that are specific to the homocysteine receptor, which would yield the anti-atherogenic effect of ethanol without the untoward side effects of ethanol ingestion.

The examples presented above are provided for illustrative purposes only and to further explain the invention. They are not intended to limit the invention in any manner. All references cited herein are hereby expressly incorporated in their entirety by reference.

For the above-stated reasons, it is submitted that the present invention accomplishes at least all of its stated objectives.

What is claimed is:

1. A method for developing a new drug for the treatment and/or prevention of atherosclerosis comprising:

assaying vascular smooth muscle cells for the ability of said drug to act as an NMDA receptor antagonist in vitro.

2. The method of claim 1 wherein said assay involves cultured vascular smooth muscle cells.

3. The method of claim 2 wherein said vascular smooth muscle cells are avian cells.

4. The method of claim 2 wherein said cells are human cells.

5. The method of claim 2 wherein said cells are rabbit cells.

6. The method of claim 1 wherein said assay further comprises:

measuring of [$^3$H] thymidine incorporation in cultured vascular smooth muscle cells in the presence of and in the absence of homocysteine.

7. The method of claim 1 wherein said assay involves RTPCR to identify the levels of c-myb and c-fos mRNA transcripts in the presence of homocysteine.

8. The method of claim 1 wherein said assay includes RNA blot analysis to identify c-fos activity.

9. The method of claim 8 wherein said RTPCR involves assaying for c-myb activity.

10. The method of claim 1 wherein said assay involves analysis of diacylglycerol synthesis.

11. The method of claim 1 wherein said assay involves determination of protein kinase C activity in the presence and absence of homocysteine.

12. The method of claim 1 wherein c-myb induction in the presence of homocysteine is measured before and after introduction of the putative anti-atherogenic agent.

13. The method of claim 1 wherein Tgfβ activity is assayed in the presence and absence of homocysteine.

14. The method of claim 1 wherein said assay includes measuring the change in intracellular calcium by fluorometry.

15. The method of claim 1 wherein said assay includes assaying for the presence of increased intracellular calcium, upregulation of jun, fos, and myb in the presence of homocysteine.

* * * * *

UNITED STATES PATENT AND TRADEMARK OFFICE
CERTIFICATE OF CORRECTION

PATENT NO. : 6,469,027 B1
DATED : October 22, 2002
INVENTOR(S) : Rosenquist et al.

It is certified that error appears in the above-identified patent and that said Letters Patent is hereby corrected as shown below:

<u>Column 1,</u>
Line 16, "(NIH-95-HL-01-H)" should read -- (HL 55940) --

Signed and Sealed this

Fifteenth Day of June, 2004

JON W. DUDAS
*Acting Director of the United States Patent and Trademark Office*